(12) United States Patent
Carlsson et al.

(10) Patent No.: US 8,874,234 B2
(45) Date of Patent: Oct. 28, 2014

(54) IMPLANTABLE DEVICE WITH IMPROVED SURFACE CHARACTERISTICS

(75) Inventors: Louise Carlsson, Vikingstad (SE); Steven Savage, Jarfalla (SE); Jens Wigenius, Hono (SE); Jessica Eriksson, Sodertalje (SE); Kenneth Dowling, Bro (SE)

(73) Assignee: St. Jude Medical AB, Jarfalla (SE)

( * ) Notice: Subject to any disclaimer, the term of this patent is extended or adjusted under 35 U.S.C. 154(b) by 0 days.

(21) Appl. No.: 13/980,284

(22) PCT Filed: Nov. 8, 2011

(86) PCT No.: PCT/EP2011/069653
§ 371 (c)(1),
(2), (4) Date: Sep. 30, 2013

(87) PCT Pub. No.: WO2012/097891
PCT Pub. Date: Jul. 26, 2012

(65) Prior Publication Data
US 2014/0018893 A1     Jan. 16, 2014

Related U.S. Application Data

(63) Continuation of application No. PCT/EP2011/050872, filed on Jan. 21, 2011.

(51) Int. Cl.
| | | |
|---|---|---|
| A61N 1/00 | (2006.01) |
| A61B 5/042 | (2006.01) |
| A61L 27/50 | (2006.01) |
| A61F 2/00 | (2006.01) |
| A61B 5/00 | (2006.01) |
| A61N 1/05 | (2006.01) |
| A61L 27/18 | (2006.01) |
| A61N 1/375 | (2006.01) |

(52) U.S. Cl.
CPC . *A61N 1/05* (2013.01); *A61N 1/375* (2013.01); *A61B 5/042* (2013.01); *A61L 27/50* (2013.01); *A61L 2400/18* (2013.01); *A61L 2400/12* (2013.01); *A61B 2562/12* (2013.01); *A61F 2/0077* (2013.01); *A61B 5/00* (2013.01); *A61N 1/056* (2013.01); *A61L 27/18* (2013.01); *A61B 2560/0406* (2013.01)
USPC ........................................................ 607/116

(58) Field of Classification Search
USPC ........................................................ 607/116
See application file for complete search history.

(56) References Cited

U.S. PATENT DOCUMENTS

| | | |
|---|---|---|
| 2003/0204229 A1 | 10/2003 | Stokes |
| 2007/0148206 A1 | 6/2007 | Demirel et al. |

(Continued)

FOREIGN PATENT DOCUMENTS

| | | |
|---|---|---|
| EP | 0259536 A2 | 3/1988 |
| EP | 0259536 A3 | 1/1989 |

OTHER PUBLICATIONS

International Search Report—Int'l App No. PCT/EP2011/096953; Int'l Filing Date: Nov. 8, 2011.

(Continued)

*Primary Examiner* — Robert N Wieland

(57) ABSTRACT

An implantable device comprises a polymer structure having an outer surface facing a surrounding tissue when the implantable device is implanted in a subject body. At least a portion of the surface of the structure has a semi-random pattern of extending micropillars. The semi-random pattern of micropillars on the surface contributes to advantageous surface characteristics of the implantable device in terms of reducing adhesion viable cells to the implantable device as compared to regular patterns of micropillars.

12 Claims, 20 Drawing Sheets

(56) References Cited

U.S. PATENT DOCUMENTS

| | | | |
|---|---|---|---|
| 2009/0024197 A1 | 1/2009 | Jensen | |
| 2011/0039033 A1* | 2/2011 | Merschrod et al. | 427/511 |
| 2013/0256944 A1* | 10/2013 | Victor et al. | 264/220 |

OTHER PUBLICATIONS

Written Opinion of the Int'l Searching Authority—Int'l App. No. PCTEP2011/096953; Int'l Filing Date: Nov. 8, 2011.

Cortese, Barbara et al., "Superhydrophobicity Due to the Hierarchical Scale Roughness of PDMS Surfaces," Langmuir. 2008;24:2712-2718.

Kidambi, Srivatsan et al., "Cell Adhesion on Polyelectrolyte Multilayer Coated Polydimethysiloxane Surfaces with Varying Topographies," Tissue Engineering. 2007;13(8):2105-2117.

Koh, Li Buay et al., "The effect of topography of polymer surfaces on platelet adhesion," Biomaterials. 2010;31:1533-1545.

Kolind, Kristian et al., "A combinatorial screening of human fibroblast responses on micro-structured surfaces," Biomaterials. 2010;31:9182-9191.

Milner, Keith R. et al., "Sub-micron texturing for reducing platelet adhesion to polyurethane biomaterials," J Biomed Mater Res. 2006;76A:516-570.

\* cited by examiner

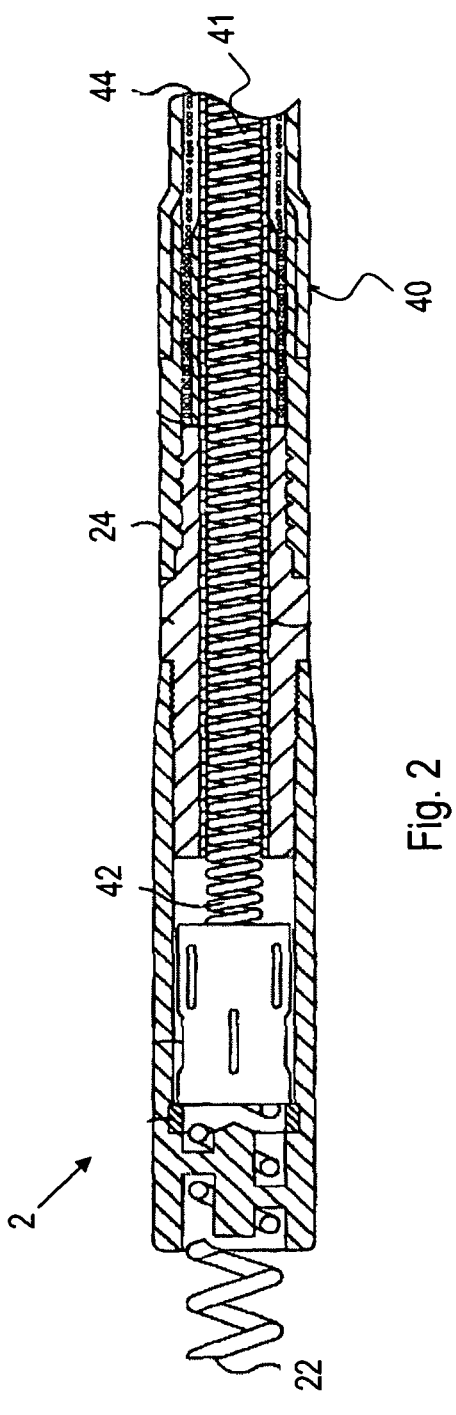
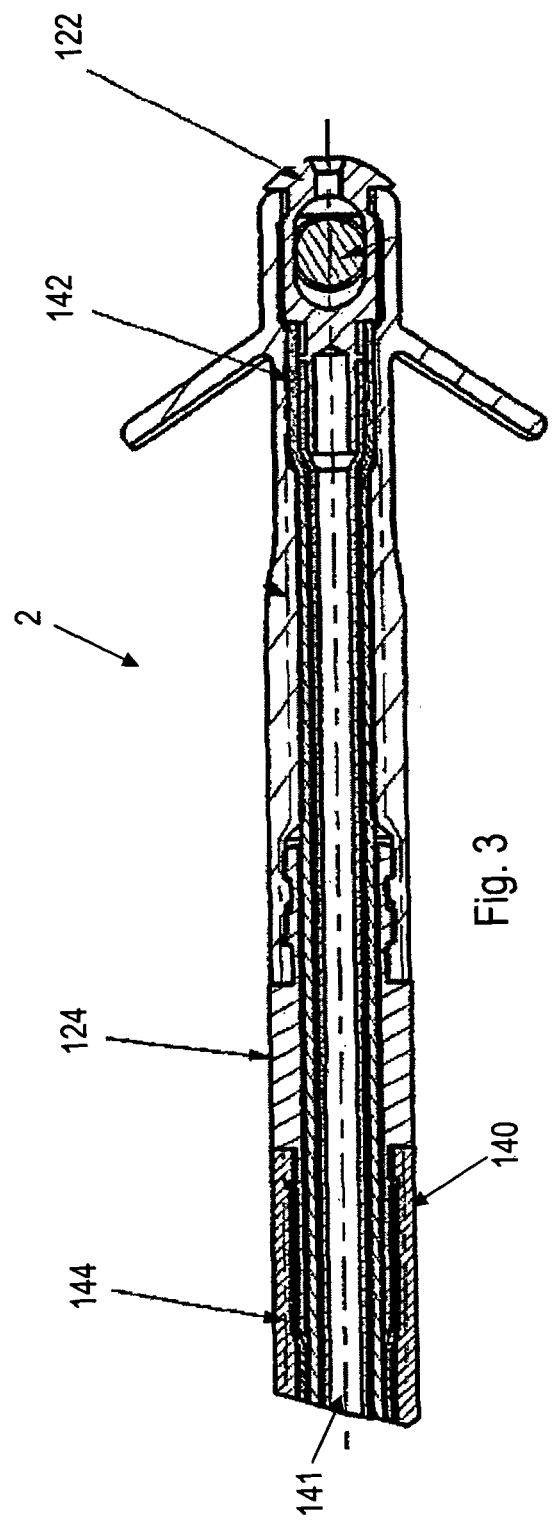
Fig. 2
Fig. 3

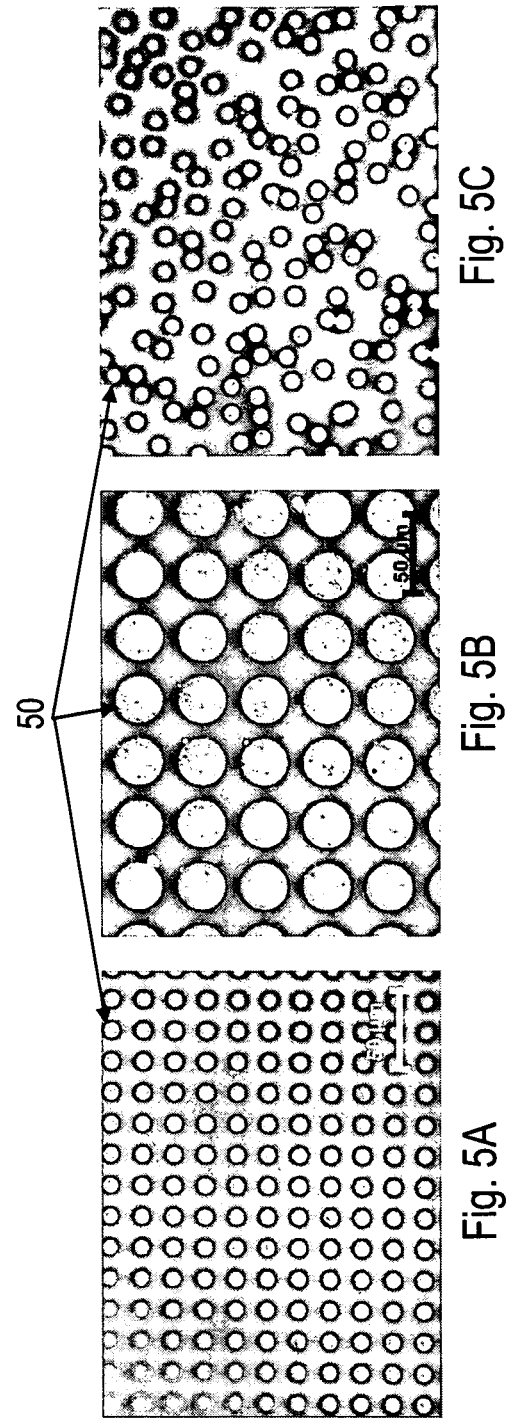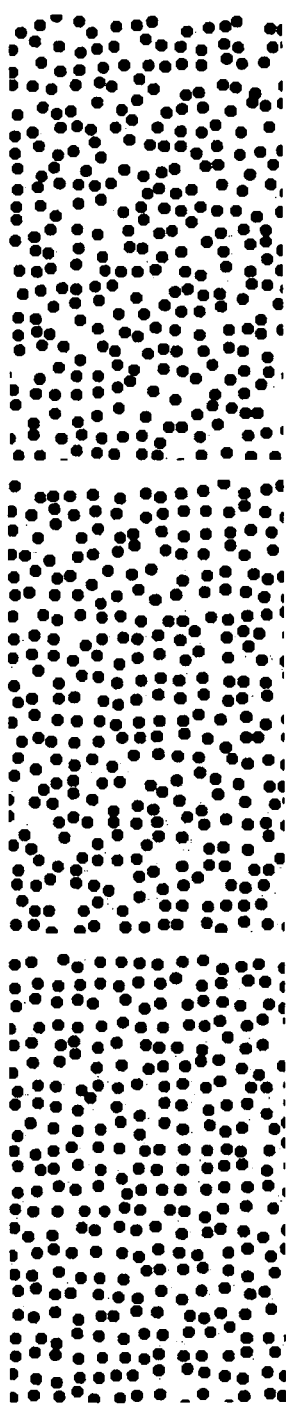

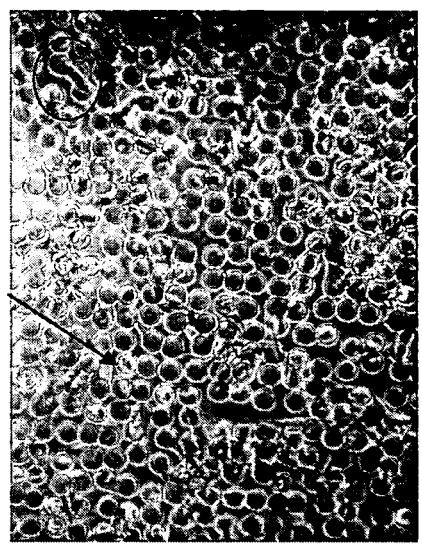
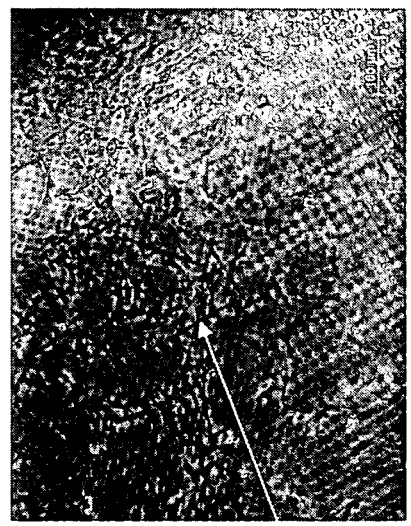
Fig. 19B
Fig. 19A

IMPLANTABLE DEVICE WITH IMPROVED SURFACE CHARACTERISTICS

CROSS REFERENCE TO RELATED APPLICATION(S)

This is a U.S. national stage application of International Application No. PCT/EP2011/069653, filed Nov. 11, 2011, which claims priority of Application No. PCT/EP2011/050872, filed Jan. 21, 2011.

TECHNICAL FIELD

The present invention generally relates to implantable devices, and in particular to an implantable device with improved surface characteristics to reduce protein adsorption and/or cell adhesion to the surface of the implantable device.

BACKGROUND

Implantable devices come in a range of variants with varying geometrical sizes, materials and functions. Implantable devices include implantable medical devices (IMDs), such as cardiac pacemakers, cardiac defibrillators or cardioverters, implantable sensors, implantable catheters and implantable medical leads.

When implanting an implantable device a shell of water molecules will be created around the implanted material surface within nanoseconds. Shortly after this initial hydration layer, blood proteins and other macromolecules arrive at the surface. The protein adsorption process is dependent on the capability of the protein molecules to displace the tightly or loosely bound hydration layer. Depending on the interaction between the surface of the implantable device and the proteins the adsorption often causes conformational change of the proteins. This is of importance since the conformation changes can expose hidden epitopes, which may be responsible for initiating reactions such as inflammation, coagulation and foreign body response that eventually may lead to fibrous encapsulation. Also various cells are recruited and adhere to the surface of the implantable device, possibly via the adsorbed proteins. As a consequence, a thrombus is formed due to the accumulation of blood components including proteins and cells. The thrombus will over time start to fibrose and calcify into a tough fibrous capsule. This process causes the implantable device to adhere to the tissue, as for example the vascular wall. The tissue adherence will increase the risk of damaging the tissue when extracting the implanted device.

Thus, there is a general need to improve the surface characteristics of implantable devices to reduce protein adsorption and/or cell adherence and thereby reduce any risks associated with explanting the implantable device from a patient body.

Kolind et al., *Biomaterials* 31: 9182-9191 (2010) discloses the effect of surfaces structured with topographical features and their influence on cellular behavior. The article concludes that altering the interpillar gap size of the structures revealed a significant change in fibroblast proliferation, where larger interpillar gap sizes reduced fibroblast proliferation on Si-wafers coated with a surface layer of tantalum oxides.

Koh et al., *Biomaterials* 31: 1533-1545 (2010) investigates the influence of surface topography on fibrinogen and platelet adsorption on poly(lactic-co-glycolic-acid) films. The article concludes that low levels of fibrinogen adsorption and platelet response are achieved with surface structures having high aspect ratio with reduced interspacing or high density.

Milner et al., *Journal of Biomedical Materials Research, Part A* 76(3): 561-570 (2006) discloses platelet adhesion to polyether (urethane urea) surfaces textured with two different sizes of submicron pillars. The authors concluded that optimization of the pillar geometries could lead to a decrease in platelet adhesion by reducing the accessible surface area of the polyether (urethane urea) surface.

Kidambi et al., *Tissue Engineering* 13(8): 2105-2117 (2007) demonstrates that micro-topography of the surface of polydimethylsiloxane (PDMS) surfaces with poly(diallyldimethylammonium chloride)/sulfonated poly(styrene) coating influences cell adhesion and proliferation is dependent on pattern size and pitch.

Cortese et al., *Langmuir* 24(6): 2712-2718 (2008) discloses a hierarchical micro- and nanostructured polydimethylsiloxane superhydrophobic surface with tuned wettability.

US 2007/0148206 discloses a nanoengineered sculptured thin film of para-xylylene derivative polymer that can be used on implantable devices to prevent fibrous encapsulation and infections on the film. The document, though, also mentions that the film promotes cell differentiation, proliferation and adhesion.

The above described documents discuss various solutions related to the problem of protein adsorption and/or cell adhesion to surfaces. There is, though, still room for improvements within the technical field of implantable devices in terms of optimizing surface characteristics.

SUMMARY

It is a general objective to provide an implantable device having improved surface characteristics.

This and other objectives are met by embodiments as disclosed herein.

An aspect of the embodiments relates to an implantable device comprising a structure made of a material selected from silicone, polyurethane and combinations thereof. The structure has a surface facing the surrounding tissue when the implantable device is implanted in a subject's body. At least a portion of the surface of the structure has a pattern of extending micropillars. According to the embodiments the micropillars are arranged on the surface in a semi-random pattern where the coordinates of a micropillar number i on the surface are defined as $(x_i, y_i) = (x_i^0 + \alpha_i \times \zeta \times s, y_i^0 + \beta_i \zeta \times S)$. The parameters $\alpha_i$, $\beta_i$ are random numbers within a range of 0 to 1 and the parameter S denotes an average interpillar spacing in the semi-pattern of micropillars. The randomness parameter $\zeta$ is within a range of 0.2 to 0.9 and $(x_i^0, y_i^0)$ indicates the coordinates of the micropillar number i in a perfectly ordered array of extending micropillars with interpillar spacings equal to S.

The arrangement of the micropillars in the form of a semi-random pattern on the surface contributes to improved surface characteristics to the implantable device in terms of reducing cell adhesion to the surface as compared to regular patterns of micropillars.

BRIEF DESCRIPTION OF THE DRAWINGS

The invention, together with further objects and advantages thereof, may best be understood by making reference to the following description taken together with the accompanying drawings, in which:

FIG. 2 is cross-sectional view of a distal portion of an implantable medical lead according to an embodiment;

FIG. 3 is a cross-sectional view of a distal portion of an implantable medical lead according to another embodiment;

FIGS. 4A to 4C schematically illustrate semi-random patterns with varying degrees of randomness, which can be applied to the extending micropillars according to different embodiments;

FIGS. 5A to 5C are microscope images of patterns of extending micropillars according to different embodiments;

FIGS. 19A and 19B are microscope images of fibroblast cells cultured on a surface with an ordered pattern of extending microstructures (FIG. 19A) and on a surface of semi-random pattern of extending microstructures (FIG. 19B);

DETAILED DESCRIPTION

Figure 1:
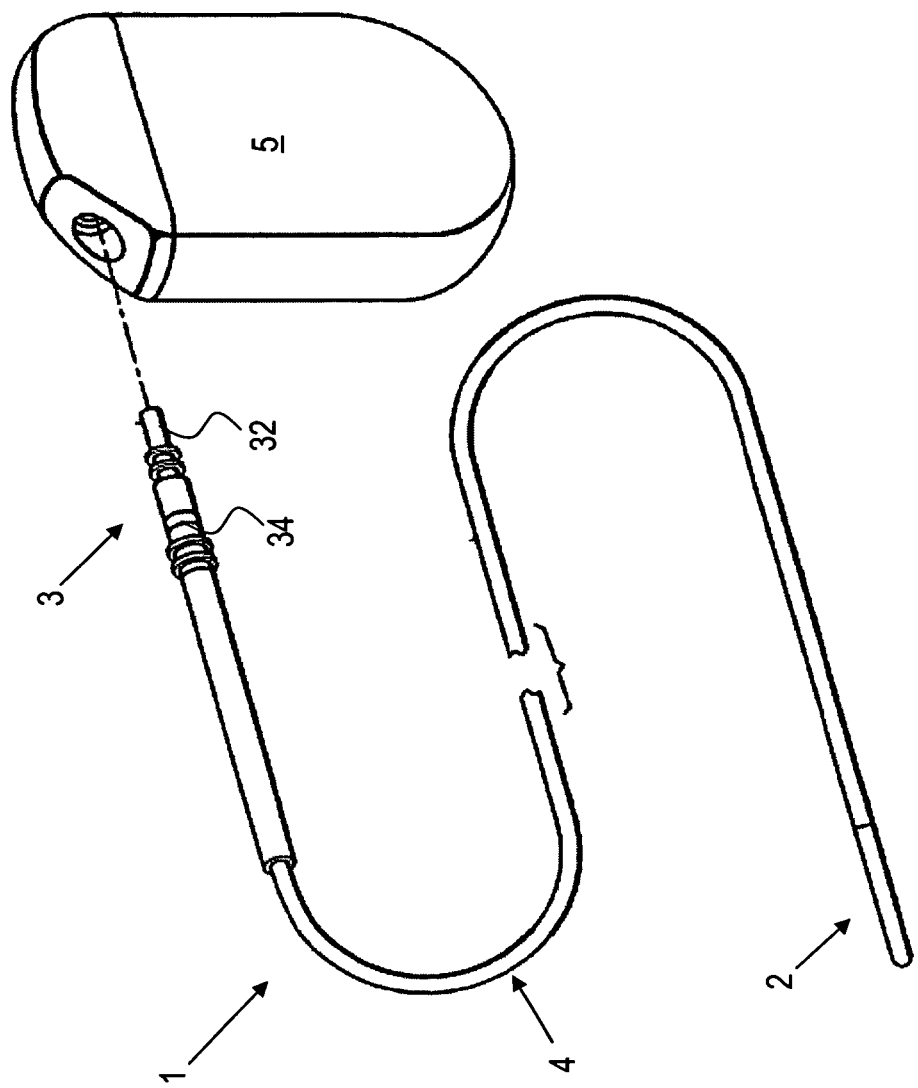
FIG. 1 is a schematic overview of an implantable medical lead connectable to an implantable medical device.

Throughout the drawings, the same reference numbers are used for similar or corresponding elements.

The embodiments generally relate to implantable devices and in particular to such implantable devices having improved surface characteristics that affect the protein adsorption and/or the cell adhesion to the surfaces of the implantable devices.

An implantable device is any device designed to be implanted in an animal body, preferably mammalian body and more preferably a human body of a subject. There the implantable device will exert an intended function, such as diagnosis, monitoring and/or therapy, depending on the particular type of implantable device. Non-limiting examples of implantable devices include so-called implantable medical devices (IMDs). There are several variants of IMDs that are traditionally implanted in the human body to exert an intended diagnosis and therapy. Examples of such IMDs include pacemakers, defibrillators and cardioverters, which all are directed towards providing therapy to a subject's heart. IMDs need, however, not be limited to cardiac-associated IMDs but may also include other implantable medical devices, such as drug pumps, neurological stimulators, physical signal recorders, various sensors, such as pressure sensors, oxygen sensors, glucose sensors, etc. Further examples of implantable devices that are traditionally employed are implantable catheters and implantable medical leads. Such implantable devices could be implanted alone but are generally connected to an IMD. For instance, implantable medical leads are traditionally connected to pacemakers, defibrillators or cardioverters in order to provide the electrical connection between sites in connection with the subject's heart and the pacemaker, defibrillator or cardioverter, which is generally implanted remotely from the heart in the subject body.

The implantable device is generally intended to be left in the subject body for some time, ranging from some weeks or months up to several years or even the whole life time of the subject.

When implanting the implantable device in the subject body the outer surfaces of the implantable device will be exposed to molecules, such as proteins and other macromolecules, and cells of the subject's body. As a consequence and which has been discussed in the background section, the implantable device is typically embedded in a protein and cell layer, such as thrombus or fibrin clot. This accumulation of proteins and cells on the surface of the implantable device can have several negative consequences. Firstly, a fibrin clot can cause the implantable device to adhere to surrounding tissue, such as the vascular wall when an implantable medical lead runs through a blood vessel in the subject's body. If the implantable medical lead is to be explanted and removed from the subject body the tissue adherence can lead to problems in terms of risks of damaging the tissue when extracting the implantable device from the body. Secondly, the fibrin clot can interfere with the function of the implantable device. For instance, implantable sensors can operate according to various embodiments, including optical measurements, chemical reactions, etc. In such a case, a fibrin clot formed around the sensor may interfere with the sensor reading and the optical measurements or chemical reactions. Thus, there is a general need within the art of providing implantable devices having improved surface characteristics that reduce or inhibit protein adsorption and/or cell adhesion to the surface of the implantable device.

A general aspect of the embodiments relates to an implantable device comprising a structure made of a material selected from silicone, polyurethane and combinations thereof. These insulating materials are commonly employed among implantable devices and have favorable properties in terms of being non-toxic, flexible, electrically insulating, etc. Combinations of silicone and polyurethane include any combinations of the two materials in any desired proportions. Particular preferred such combinations are co-polymers of polyurethane and silicone. Such co-polymers of polyurethane and silicone are available on the market under various trade names, such as Optim® and Elast-Eon™. Optim® is a methylene diisocyanate (MDI) based silicone-polyurethane copolymer containing about 60% of a silicone-rich macrodiol blend and chain-extended with 1,4-butanediol. The macrodiol consists of about 80% bis-hydroxy-ethoxy-propyl-polydimethylsiloxane and about 20% polyhexamethylene oxide. The resulting co-polymer of polyurethane and silicone has mechanical strength and abrasion resistance of polyurethane and the rubbery flexibility of silicone. The co-polymer is highly biostable, soft and flexible and also has low surface friction. The co-polymer of polyurethane and silicone may additionally comprise other components, such as components to compatibilize the polyurethane and silicone precursors. A non-limiting example of a particular resulting co-polymer of polyurethane and silicone consists of 48% silicone rubber, 40% polyurethane and 12% of polyhexamethylene oxide (PHMO). The percentages presented above are weight percentages unless otherwise indicated. Other ratios of these components are possible to achieve a broad range of mechanical properties.

Other preferred co-polymers of polyurethane and silicone that can be used as polymer material according to the embodiments include co-polymers of silicone, polyurethane and polycarbonate. Such co-polymers are available on the market under the trade name ECSil™. ECSil™ polymer materials are available at various relative concentrations of their including polymers resulting in different tear strength, tensile strength and modulus of elasticity of the polymer material. A particular suitable co-polymer of silicone, polyurethane and polycarbonate is ECSil™ 75A. ECSil™ 75A is a polycarbonate urethane copolymer with silicone rubber. It contains 60% silicone-carbonate soft segments and the silicone content is about 50%. Co-polymers of silicone, polyurethane and polycarbonate that can be used according to the embodiments are further disclosed in WO 98/54242.

The structure of silicone, polyurethane or a combination thereof has an outer surface facing surrounding tissue when the implantable device is implanted in a subject body. The improved surface characteristics of the embodiments are then achieved in the outer surface of the structure. This means that at least a portion of the surface of the structure has a pattern of extending micropillars arranged in the surface and extending out from the surface. According to the embodiments, these micropillars are arranged in a semi-random pattern of extending micropillars. This is in contrast to the prior art where a regular pattern of micropillars have been used. However, experimental results presented herein indicate that a semi-random pattern of extending micropillars is preferred in terms of reducing the number of viable cells adhering to the surface. In such a case, the coordinates $(x_i, y_i)$ of a micropillar number i on the surface are preferably defined as $(x_i, y_i) = (x_i^0 + \alpha_i \times \zeta \times S, y_i^0 + \beta_i \times \zeta \times S)$. The parameters $\alpha_i$, $\beta_i$ are random numbers within a range of 0 to 1 and S denotes an average interpillar spacing in the semi-pattern of micropillars. In an embodiment, the random numbers follow a normal distribution implying that values around 0 are generally generated more often as compared to values close to 1. The randomness parameter $\zeta$ is selected within a range of 0.2 to 0.9, preferably within a range of 0.5 to 0.7 and more preferably equal to 0.6. Finally, $(x_i^0, y_i^0)$ indicates the coordinates of the micropillar number i in a perfectly ordered array of extending micropillars with interpillar spacings equal to S.

The particular counter i then goes through one up to N for a pattern having N micropillars.

Without being bound by theory, the semi-random pattern is believed to reduce the number of viable cells adhering to the surface by preventing the build up of any organized and uniform pattern of cells on the surface, such as in the surface area between the micropillars. The semi-randomness of the organization of the micropillars on the surface breaks the uniform interpillar area. This means that the semi-randomness will generally create areas on the surface between micropillars where one or a few cells can adhere. However, these areas on the surface will be isolated by other areas on the surface where the interpillar spacing or distance will be too small to allow cells to adhere to the surface in the area between the micropillars. The isolation of cells or small clusters of cells, such as fibroblasts, implies that the cells cannot effectively connect and communicate with each other. The lack of sufficient intercell connections is believed to be a major contribution to the reduced viable cell adhesion seen by having a semi-random pattern of extending micropillars on the surface. The cells could then trigger apoptosis or otherwise be negatively effected in terms of their viability, which reduces or inhibits the build-up of a fibrin clot and connective tissue around the implantable device.

The semi-random pattern of extending micropillars is preferably selected to prevent micropillars from being positioned on substantially the same coordinates on the surface. In such a case, micropillars could be arranged very close to each other in clusters basically together forming larger pillar structures. These larger pillar structures will then have an overall diameter or overall side lengths that could result in several cells adhering onto the structure top and form viable colonies. This is generally not preferred since such viable colonies may contribute to the formation of connective tissue and fibrin clots around the implantable device.

Hence, in an embodiment the distance between the coordinates $(x_i, y_i)$ of a micropillar number/on the surface and the coordinates of a closest neighboring micropillar on the surface is preferably larger than the average pillar diameter or the average pillar side lengths. In such a case, micropillars will be prevented from forming larger structures on the surface.

In an embodiment, the micropillars in the semi-random pattern have an average pillar diameter within a range of 20 μm to 40 μm in the case of cylindrical micropillars. The embodiments are, however, not limited to cylindrical micropillars but also encompass micropillars having non-circular cross-sections including micropillars with oval, rectangular, quadrilateral, quadratic or rhombic cross-sections. In such a case, the average length of the pillar sides of the rectangular, quadrilateral, quadratic or rhombic micropillars is within the range of 20 μm to 40 μm. Quadratic and rhombic micropillars have four pillar sides of the same length, which is within the range of 20 μm to 40 μm. A rectangular micropillar has two opposite pillar sides of the same the length and two other opposite sides of the same length. The average lengths of these sides are within the range of 20 μm to 40 μm. Correspondingly, a quadrilateral micropillar can potentially have four pillar sides of different lengths. In such a case, preferably all these side lengths are within the range of 20 μm to 40 μm. Oval micropillar preferably have both axes in the range of 20 μm to 40 μm.

The average pillar diameter, average pillar side lengths or average oval axis lengths are within the defined interval of 20

μm to 40 μm. When manufacturing micropillars, i.e. with dimensions in the μm-range, the manufacture method will generally inherently cause a distribution of the pillar diameter or the pillar side lengths around the average value within the interval of 20 μm to 40 μm. However, the average diameter or average pillar side lengths are still within the defined interval. In a preferred embodiment, a majority of the micropillars formed on the surface have pillar diameter or pillar side lengths within the defined interval, preferably at least 80% of the micropillars, more preferably at least 90%, such as at least 95% of the micropillars have a diameter or side lengths within the interval of 20 μm to 40 μm.

Experimental data presented herein have demonstrated that the particular diameter or side length interval of 20 μm to 40 μm is advantageous in terms of reducing or inhibiting the adherence of viable cells to the surface. It is seen from the experimental results that cells coming into contact with the surface climb up to the top of the micropillars. The area of the micropillar tops is, due to the careful selection of the average diameter or average side length interval, close to, or slightly smaller or larger (depending on cell type) the average size of relevant cells involved in the formation of the fibrous capsule. In particular fibroblasts constitute key cells in wound healing and the embedding of implantable devices in connective tissue and fibrous capsules. The average size of such fibroblast cells is about 500-550 μm$^2$, i.e. close to or slightly smaller than the pillar top area.

Without being bound by theory, a further improvement to the surface characteristics of the embodiments with semi-random pattern can be achieved with the above preferred micropillar diameter or side lengths. This further improvement might be due to that fibroblasts and other cell types climb onto the micropillars and reach the micropillar tops. From there the cells cannot proceed further and become isolated from other cells. The lack of cell-to-cell contacts for the cells adhering to the micropillar tops means that the cells subsequently will die, possibly due to induced apoptosis. The careful selection of the micropillar diameter or side lengths will hence cause a cell trap, in particular for fibroblasts, causing isolation of the cells on the pillar tops, where the cells will not survive well. This reduced viability of any adhering cells will lead to desired surface characteristics, and, for instance, facilitate explanation of the implantable device.

A particular embodiment relates to a structure of the implantable device having at least a portion of its outer surface covered with a semi-random pattern of extending cylindrical micropillars having an average pillar diameter in the range of 20 μm to 40 μm. The average diameter of the micropillars is preferably within the range of 25 μm to 35 μm and more preferably equal to about 30 μm.

The height of the micropillars is within the μm-range, hence, the expression "micropillars". The micropillars could have fairly short average heights, for instance from a few micrometers. The maximum average pillar height is generally dictated by stability and manufacture limitations. Thus, it is typically hard to manufacture very tall micropillars if the average diameter or average side lengths are to be within the range of 20 μm to 40 μm. In such a case, the micropillars will easily break either during manufacture or post-manufacture handling of the implantable device. Therefore average pillar heights over 100 μm are seldom practical. In an embodiment, the micropillars have an average pillar height within a range of 2.5 μm to 30 μm, preferably within a range of 4 μm to 25 μm. Experiments have successfully been conducted with micropillars having an average pillar height within the range of 4 μm to 5 μm.

At least a portion of the (outer) surface of the structure in the implantable medical device has the semi-random pattern of extending micropillars. It is generally preferred if the whole or at least a majority part of the outer surface has the semi-random pattern of micropillars.

The semi-random pattern on the outer surface of the structure in the implantable device can, in an embodiment, be a hierarchical semi-random pattern of the micropillars and of nanostructures formed on and extending from the micropillars. The pattern is hierarchical in terms of providing both structures in the μm-range, i.e. the micropillars, and in the nm-range, i.e. the nanostructures. According to an embodiment, the nanostructures may have an average height within a range of 20 nm to 140 nm, preferably within a range of 60 nm to 100 nm. A hierarchical pattern generally increases the hydrophobicity of the surface to thereby form a so-called superhydrophobic surface. Superhydrophobicity could have a positive effect in terms of reducing protein adsorption and cell adhesion to the surface.

The relevant structure of silicone, polyurethane or a combination thereof, which as a surface with a semi-random pattern of extending micropillars, could be any structure of an implantable device. For instance, implantable medical leads and implantable catheters typically have a lead body of an insulating tubing running substantially from one end to the opposite end of the lead or catheter. This insulating tubing could then advantageously be the structure having an outer surface, i.e. lateral surface, with a semi-random pattern of extending micropillars. In other implantable devices also structures other than tubes could be made of silicone, polyurethane or a combination thereof and could therefore be provided with a semi-random pattern of micropillars according to the embodiments. It is also possible to cover or coat metallic structures or structures of other materials besides silicone, polyurethane or combinations thereof with a thin coating or layer of silicone, polyurethane or a combination thereof with an outer surface having a pattern of micropillars. The reason for this coating could be to impart the desired surface characteristics also to other parts of an implantable device that are not made of silicone, polyurethane or a combination thereof to reduce protein adsorption and/or cell adhesion to also these other parts. For instance, an implantable pressure sensor could be in the form of a structure of a piezoelectric material. In such a case, the outer surface of the piezoelectric structure could be coated with a thin layer of silicone, polyurethane or a combination thereof with an outer surface having a semi-random pattern of micropillars in order to reduce build up of connective tissue or fibrin clots onto the piezoelectric structure, which then could interfere with the function of the pressure sensor. Also the body of a pacemaker, defibrillator or cardioverter, which is typically denoted can or case in the art, could be coated with a thin layer of silicone, polyurethane or a combination thereof with a semi-random pattern of micropillars.

It is desirable to reduce the thickness of the fibrous capsule that grows around an implantable medical device, such as pacemaker. A possible solution is to apply a coating of the silicone, polyurethane or combination thereof with a semi-random pattern of micropillars to the outer surface of the implantable medical device as mentioned above. Another possibility is to form a pocket or pouch of silicone, polyurethane or a combination thereof having a semi-random pattern of micropillars on its outer surfaces. The implantable medical device can then be placed in the pocket when implanted in the subject's body.

In these embodiments, the patterned surface of the coating or the pocket will reduce the amount of fibrous and connective tissue around the implantable medical device. Hence, the surgical operation of replacing the implantable medical device will be simplified. Additionally, since the encapsulation of the implantable medical device in connective tissue can be reduced according to the embodiments, the esthetical appearance of the implantable medical device under the skin will improve since the implantable medical device will be less obvious under the skin.

FIG. 1 is a schematic illustration of an implantable device according to an embodiment, exemplified by an implantable medical lead 1. The implantable medical lead 1 has a so-called distal end 2 adapted to be introduced into a suitable pacing site to enable delivery of pacing pulses and sensing electric activity of the tissue, such as heart, at the particular pacing site. At least one electrode, generally denoted pacing and sensing electrode in the art, is arranged in connection with the distal end 2. It is this electrode that delivers pacing pulses to the tissue and captures electric signals originating from the tissue.

An opposite or proximal end 3 of the implantable medical lead 1 is configured to be mechanically and electrically connected to an IMD 5. The IMD 5 can be any implantable medical device used in the art for generating and applying, through the implantable medical lead 1, electric pulses or shocks to tissues. The IMD 5 is advantageously a pacemaker, defibrillator or cardioverter to thereby have the implantable medical lead 1 implanted in or in connection to a ventricle or atrium of the heart.

The proximal end 3 comprises at least one matching electrode terminal 32, 34 that provides the electric interface of the implantable medical lead 1 towards the IMD 5. Thus, each electrode terminal 32, 34 is connected to a respective connector terminal in the IMD 5 to thereby provide electric connection between the IMD 5 and the at least one electrodes through the at least one electrode terminal 32, 34 and at least one conductor, to be further described herein.

The implantable medical lead 1 typically comprises a respective electrode terminal 32, 34 for each electrode in connection with the distal end 2.

The implantable medical lead 1 also comprises a lead body 4 running from the proximal end 3 to the distal end 2. This lead body 4 comprises an insulating tubing having a bore. This bore is designed and dimensioned to house the at least one conductor.

According to the embodiments, the insulating tubing is made of a material selected from silicone, polyurethane or a combination thereof. Furthermore, at least a portion of the lateral surface of the insulating tubing has a semi-random pattern of extending micropillars as defined herein.

FIG. 2 illustrates a greatly enlarged cross-sectional view of an embodiment of the distal end 2 of an implantable medical lead of the active fixation type. As seen, the implantable medical lead has an outer flexible insulating tubing 40 made of silicone rubber, polyurethane or a combination thereof and having a lateral surface with the semi-random pattern of extending micropillars. The outer insulating tubing 40 covers a first coiled conductor 44. The conductor 44 extends along through the lead body and terminates in connection with the distal end 2, where it is electrically coupled, for example by spot or laser welding, to a ring electrode 24.

Extending along the length of the lead body through the ring electrode 24 is a second coiled conductor 42, which is insulated from the outer coiled conductor 44 by an inner insulating sheath or tubing. The inner conductor 42 terminates at a substantially cylindrical crimp bus. The crimp bus is coupled to the fixation helix 22. The fixation helix 22 has the dual function of fixing the implantable medical lead to the myocardium or other target tissue and functions as a sensing/pacing electrode.

In an alternative embodiment of an active fixation lead, the ring electrode is omitted. In other words, the lead is of the unipolar type. The electrode is then the active helix fixation electrode or another type of active fixation electrode.

FIG. 2 also illustrates the bore 41 of the insulating tubing 40, in which the first and second coil conductors 42, 44 are running.

The implantable medical lead must not necessarily be of a so-called active fixation type. FIG. 3 illustrates an enlarged cross-sectional view of an implantable medical lead of passive fixation type. The lead body has the outer flexible insulating tubing 140 made of silicone, polyurethane or a combination thereof and has a semi-random pattern of extending micropillars on its lateral surface. The insulating tubing 140 has a bore or channel 141 housing a first coiled conductor 144 extending along the lead body and terminating at a ring electrode 124 or is electrically coupled to the ring electrode 124 through a crimp sleeve (not illustrated).

A second inner coiled conductor 142 is electrically insulated from the first conductor 144 by an inner insulating sheath or tubing. The inner conductor 142 is electrically connected to a tip electrode 122. Passive fixation of the implantable medical lead at a correct position in a patient body is achievable by a tine assembly.

It is anticipated that the implantable medical lead partly illustrated in FIG. 3 may alternatively be of a unipolar type. In such a case, the ring electrode 124 and its associated coiled conductor 144 can be omitted.

The semi-random patterns of extending micropillars can be formed on the surface of the structure of silicone, polyurethane or a combination thereof according to various techniques. Non-limiting examples of such techniques include various so-called microfabrication techniques, including laser-based or direct techniques and embossing or replication techniques.

Photolithography is the most widely used form of lithography, which originally is a process in which a design is transferred from a master onto a substrate surface. In photolithography a photoactive polymer layer is irradiated through a mask followed by developing, where either the exposed or unexposed polymer is removed, leaving a positive or negative image of the mask on the surface. The mask works as a stencil and can be used to create multiple copies with the same pattern design. It generally consists of a UV-transparent glass with an absorber, usually a metal, deposit upon it. The design of the metal pattern will determine the design of the structures, and is created in a computer aided design (CAD) software. The photoresist is an organic polymer that is sensitive to UV radiation that will during the exposure, be cross-linked. The latent resist image formed during exposure will be transformed into a relief image by development. Two main technologies are available and that is wet or dry development. The relief image will serve as the mould, used in later stage, to emboss the desired structure onto the polymer material.

The pattern of a mould can easily be transferred to a thermoplastic polymer using hot embossing. The polymer substrate is heated above its glass transition temperature (Tg). The mould is pressed onto the heated polymer for its pattern to be transferred to the substrate. The substrate is separated from the mould after the system has been cooled down below the Tg of the polymer. Typical mould materials used in hot embossing are nickel and silicon, but moulds of plastic have also been used.

An embodiment of producing a semi-random pattern of microstructures onto a surface according to the embodiments is therefore to emboss a negative of the chosen pattern on two suitable flat substrates, for example plates of hard material, such as silicon or a metal material. The plates are heated to the required temperature dictated by the glass transition temperature of the silicone, polyurethane or silicone-polyurethane combination where the polymer softens. The structure to be treated, such as insulating tubing, is placed between the plates, a force is applied and the plates are rolled relative each other. One plate may be stationary or both plates may move and the structure, such as insulating tubing, remains stationary. The pattern from the plates is thereby transferred to the outer surface of the structure, which is then removed from the plates and cooled.

Alternative methods to create the mould exist, such as deep reactive ion etching (DRIE) and wet etching in silicon.

If a hierarchical semi-random pattern is desired, different techniques can produce nanostructures on the surface, examples of these can be spin-casting of polymers, laser treatment, plasma treatment, polymer de-mixing and colloidal lithography. For instance, plasma treatment techniques can be used to modify the chemistry and the surface roughness of polymeric surfaces and it is used in biomedical area for several applications. Plasma treatments have several advantages. For example, the modification is just to the surface layer and will not influence the bulk properties and the modification is uniform over the whole surface. There are three different kinds of reactions occurring during the plasma treatment of a polymer: surface reaction, plasma polymerization and cleaning and etching. The etch reaction is similar to DRIE, which is a subtractive process typically used in the micromachining of Si and is used to create high aspect ratio features by using high density plasma with low ion energy. The kind of reaction and of which extent it occurs depends on the gas used. For example, organic groups are expected to etch much more quickly in fluorine-containing plasmas than inorganic groups. During the etch reaction non-volatile products are formed on the etched polymer surface. These are products that will behave as masking materials for the ongoing etching, and as a result, the parts of the surface that are covered by inorganic polymer components are etched much more slowly than the pure organic parts. Using fluorine-containing plasmas, such as $CF_4$ or $C_4F_8$, will not only etch the polymer surface but also produce a polymer surface that is fluorinated. The etching and fluorination seem to be parallel and competitive using such plasmas and the rates of the two reactions depend on the treatment time. It is thought that fluorination dominates over etching in the beginning, but later in the treatment the two reactions occur in parallel. This means that after a certain treatment time the surface chemical composition will not be affected but only the topography. An alternative to the $C_4F_8$ is $SF_6$, which does not leave the fluorinated layer upon the polymer.

EXPERIMENTS

1 Fabrication of Polymer Test Samples

The fabrication of the polymer pieces, the test samples, involves three main steps: the design of the structure, the fabrication of the mould and the embossing.

1.1 Design of Experiments

The factors that are chosen to be evaluated are: height, spacing, diameter, array-type and nanoheight. The four first factors, height, spacing, diameter and array-type, are factors that are connected to the fabrication of the microstructures.

TABLE 1 design matrix

| No. | Height (µm) | Diameter (µm) | Spacing (µm) | Degree of chaos | Nanoheight (rms) |
|---|---|---|---|---|---|
| 1 | 5 | 10 | 10 | 0 | 100 |
| 2 | 25 | 10 | 10 | 0 | 100 |
| 3 | 5 | 30 | 10 | 0 | 100 |
| 4 | 25 | 30 | 10 | 0 | 100 |
| 5 | 5 | 10 | 30 | 0 | 100 |
| 6 | 25 | 10 | 30 | 0 | 100 |
| 7 | 5 | 30 | 30 | 0 | 100 |
| 8 | 25 | 30 | 30 | 0 | 100 |
| 9 | 5 | 10 | 10 | 0.6 | 100 |
| 10 | 25 | 10 | 10 | 0.6 | 100 |
| 11 | 5 | 30 | 10 | 0.6 | 100 |
| 12 | 25 | 30 | 10 | 0.6 | 100 |
| 13 | 5 | 10 | 30 | 0.6 | 100 |
| 14 | 25 | 10 | 30 | 0.6 | 100 |
| 15 | 5 | 30 | 30 | 0.6 | 100 |
| 16 | 15 | 30 | 30 | 0.6 | 100 |
| 17 | 5 | 10 | 10 | 0 | 500 |
| 18 | 25 | 10 | 10 | 0 | 500 |
| 19 | 5 | 30 | 10 | 0 | 500 |
| 20 | 25 | 30 | 10 | 0 | 500 |
| 21 | 5 | 10 | 30 | 0 | 500 |
| 22 | 25 | 10 | 30 | 0 | 500 |
| 23 | 5 | 30 | 30 | 0 | 500 |
| 24 | 25 | 30 | 30 | 0 | 500 |
| 25 | 5 | 10 | 10 | 0.6 | 500 |
| 26 | 25 | 10 | 10 | 0.6 | 500 |
| 27 | 5 | 30 | 10 | 0.6 | 500 |
| 28 | 25 | 30 | 10 | 0.6 | 500 |
| 29 | 5 | 10 | 30 | 0.6 | 500 |
| 30 | 25 | 10 | 30 | 0.6 | 500 |
| 31 | 5 | 30 | 30 | 0.6 | 500 |
| 32 | 15 | 30 | 30 | 0.6 | 500 |
| 33 | 15 | 20 | 20 | 0 | 300 |
| 34 | 15 | 20 | 20 | 0.3 | 300 |
| 35 | 15 | 20 | 20 | 0.6 | 300 |

1.1.1 Determination of Degree of Chaos

The range of the degree of chaos is set from 0 up to 0.6, where 0 represents the perfectly ordered array and 0.6 the degree of chaos similar to that seen in the structure of a lotus leaf. In order to determine the degree of chaos in the structure seen in the lotus leaf a large scale SEM image of the lotus leaf taken from the literature was processed using the software ImageJ developed by the NIH and then compared with pictures with different degrees of chaos. A particle analyzing function in ImageJ was used to generate positions of the points from the SEM image by inverting the SEM image and then converting it to a binary picture. The setting for the measurements was changed to generate the central x- and y-coordinates for each of the points before the picture was analyzed. ImageJ was used to generate pictures with different degrees of chaos, examples of which are seen in FIGS. 4A to 4C, where FIG. 4A has the randomness parameter $\zeta=0.4$, FIG. 4B has $\zeta=0.5$ and FIG. 4C has $\zeta=0.6$.

Each of the points in the pictures in FIGS. 4A to 4C originates from the position in which the point would have been in a perfectly ordered array. From this position the point is randomly moved both in the x and y direction. How far the point is moved is determined by the spacing, the degree of chaos, i.e. the randomness parameter, and a random number from 0 to 1. For example if the degree of chaos is 0.6 and the spacing is 10 µm, the point will deviate from the original position with a maximum distance of 6 μm, which will be the case if the random number is 1. If the position of the point generated next in order is closer to the previous position than the value of the diameter, a new position for that point will be generated, since points that are overlapping each other are unwanted. Pictures representing degrees of chaos from 0.2 to 0.9 were compared with the picture of a lotus leaf, and the degree of 0.6 was determined to best match the chaos seen in the structure of the lotus leaf the best.

1.2 Fabrication of the Templates

The templates were ordered from Acreo AB and were manufactured as briefly discussed in the foregoing in SU-8 photoresist.

1.3 Hot Embossing

The polymer Optim® was bought in the form of dog bones, which were cut into pieces of ca 1×2 cm. The pieces were preheated to 170° C., which is close to its Tg of Optim®, in an oven for 10 minutes. It is preferred that the oven temperature does not exceed the set temperature. If it does the polymer will be heated above the critical temperature, which can cause unwanted porosity. The template was put onto a hot plate, set to 175° C., in order for it to be preheated to the Tg of the polymer. The preheated polymer piece was placed on top of the template and a pressure was applied to it. The surface of the polymer was thereby softened and the micro-structured pattern on the mould was filled with the polymer. The hot plate was turned off and the polymer was left to be cooled down below the softening temperature before the polymer was separated from the template. The pressure applied was constant during this reduction in temperature. The cooling down process was hastened by nitrogen gas blown on the arrangement. Each sample was viewed in an optical microscope in order to verify that the pattern had been correctly transferred to the Optim® piece.

1.4 Plasma Treatment

Plasma treatment was carried out in Oxford Instrument Plasma lab systems 100 ICP 180 etch system. Prior to the $C_4F_8$ treatment an argon treatment was performed, which is thought to create stable free radicals on the polymer surface. The free radicals on the surface will react with the F-containing plasma radicals. The sample was placed into a chamber, which was evacuated to the set pressure for the pre-treatment of argon, which was 40 mTorr. The argon was introduced at a flow rate of 50 standard cubic centimeters per minute (sccm), and the glow discharge was ignited at 200 W. The inductive coupled plasma (ICP) power was not in use in the argon pre-treatment. The argon treatment was continued for 5 min and followed by the $C_4F_8$ treatment. The chamber was evacuated to 20 mTorr and $C_4F_8$ was introduced at a flow rate of 25 sccm. The glow discharge was ignited at 150 W. A combination of this relative low pressure and high RF-power was considered to be a hard plasma treatment and in studies seen in literature this kind of treatment has been required to create columnar-like structures.

Two protocols were used to produce two different nano-heights: one low height and one high height. In former studies the exposure time has seen to be a parameter to affect the height and the roughness. An idea is therefore to change this parameter to evaluate the roughness and find the three different protocols. Since the etching and fluorination are thought to be parallel and competitive, changing the exposure time might not only affect the surface roughness but also the surface chemistry, however changing only the ICP-power is thought to be a parameter only affecting the surface roughness. Treatment with ICP-power 500 W will be referred to as high and treatment with ICP-power 300 W will be referred to as low herein.

TABLE 2

Protocols for plasma treatment.

| Parameter | Argon | Low | High |
|---|---|---|---|
| Exposure time | 5 min | 10 min | 10 min |
| Pressure | 40 mTorr | 20 mTorr | 20 mTorr |
| RF power | 200 W | 150 W | 150 W |
| ICP power | 0 | 300 W | 500 W |
| Gas flow | 50 sccm | 25 sccm | 25 sccm |
| Temperature | 5° C. | 5° C. | 5° C. |
| Helium backing | 10 | 10 | 10 |

2 Surface Characterization

The modified Optim® surfaces were analyzed with optical microscopy.

2.1 Light Microscopy

An optical microscope was used to evaluate the height of the pillars, which was done for one sample. The height could be measured by means of focusing on top of the structures and the bottom of the structures and thereby measuring the distance. A series of images was taken with different focal depths to create a topographical profile of the surface. It was assumed that each of the other samples was embossed with the same performance and the embossing was controlled by viewing each sample in a microscope in order to verify that the structured had been embossed correctly.

2.2 Atomic Force Microscopy (AFM)

The nanostructures on the polymer surface were characterized by AFM. The surface structure of the plasma treated polymer samples was characterized by a digital instrument AFM nanoscope dimensions 3100 ran in tapping mode. The sample was placed on a plate and immobilized by vacuum suction, and loaded into the instrument. The tip was approached to surface by manually moving the probe down to ca 1 mm above the sample. When the surface was in focus, the system itself approached the surface until it interacted with the surface whereupon the measurement was started. The scan size was set to 5×5 μm and samples/line to 256. The AFM images were analyzed by using the software n-Surf.

3 Protein Adsorption

Protein adsorption of human fibrinogen (Hfg) and human serum albumin (HSA) onto processed Optim® surfaces was evaluated by ELISA. Briefly, the samples were placed in Petri dishes and a packing cut from a PDMS film was placed upon each Optim® piece in order to produce something similar to an incubation well. The dimension of the wells was 6.4 mm in diameter and approximately 1.5 mm deep and thus had a volume of ca 50 μl. The different surface structures and negative and positive control were incubated with 0.1 mg/ml Hfg respectively 0.1 mg/ml HSA for 20 min at 37° C. Both the negative and the positive control were non-processed Optim® pieces, i.e. smooth surface. The negative control was incubated with the opposite protein. In other words, in the series of Hfg the negative control was incubated in HSA and in the series of HSA the negative control was incubated in Hfg. After the incubation the samples were rinsed 5 times with washing buffer (0.1% Tween-20 in PBS) to remove unbound protein. Horse radish peroxidase (HRP) conjugated goat anti-Hfg antibody respectively HRP conjugated anti-HSA antibody was diluted in PBS to 1:20 000 for anti-Hfg and 1:10 000 for anti-HSA. 50 µl of the antibody solution was added to each well and incubated for 20 min at 37° C. After the incubation the samples were rinsed with washing buffer, five times, in order to remove any unbounded antibodies. The packing was removed from the Optim® pieces in order to eliminate the contribution from the protein adsorption on the sidewall of the wells. 30 µl of the colorimetric agent 3,3'5,5'-tetramethylbenzidene (TMB) was added on top of the structures and incubated in the dark for 10 min. TMB solutions was then pipetted to a 96-microwell plate and the absorbance values of the solutions were measured at 370 nm and 655 nm.

4 Cell Culture

The human fibroblast cell line MRC-5 was used to investigate the cell response on the different structured polymer surfaces.

A total of 17 Optim® pieces were evaluated. Each of the samples was placed in Petri dishes. Cells were prepared and cultured in cultivation flask days before the analysis. The cells were removed from the surfaces using trypsin, which makes the cells contract and de-attach from the surface. Fresh culture medium was added to the cultivation flasks and the solution was transferred and equally divided between two Petri dishes. Additional culture medium was added to completely fill the dishes. The samples were stored at 37° C. and 5% $CO_2$ for optimal condition for cell culture. The samples were observed daily and the culture medium was replaced by fresh if needed. After 24 hours the samples were investigated under an optical microscope to verify that cells were healthy and grew as expected. The culture was ended after about 3 days and images of each sample were recorded using an optical microscope. Images of separate samples were recorded after 3 and 7 days in culture.

The growth and viability were evaluated by morphological changes, cell size and density of cells. The area of the cells was measured using the outline application in AxioVison LE, the program used to record the images, and the cells were counted using the cell counter application in ImageJ.

4.1 Platelet Adhesion

Fresh blood was drawn from a healthy individual and collected in test tubes. The blood was centrifuged for 15 min in order to separate plasma and serum. The plasma was collected and transferred to another test tube. 50 µl of the plasma was added on top of the sample surfaces in the same manner as for the protein adsorption test. In other words the packing of PDMS was used even for this experiment. The plasma was incubated in 37° C. for 30 min and each sample was washed with PBS three times. During the incubation the test-samples were put on a shaker. The samples were then viewed by optical microscopy and images were recorded for each sample.

5 Results

The embossing of the 5 µm and 15 µm high structures worked out well. Problems were encountered when the 25 µm high structures were embossed and the smaller features, the 10 µm sized pillars, were seen to be cut off during the de-embossing step or the removal of the Optim® piece. The embossing process were therefore tried to be optimized in order to fabricate satisfactory pieces with this pillar height. Parameters that were considered to be changed were the thermal cycle, i.e. the difference between the embossing and the de-embossing temperature, and the time for the pressure to be applied. Different de-embossing temperatures were tried and it was found that when the temperature was higher than 135° C. the Optim® polymer was still too soft and adhered to the mould. Temperatures below this critical temperature seemed to work well as de-embossing temperature. An increase of the de-embossing temperature was thought to minimize the difference in thermal expansion of the SU-8 polymer and the Optim® polymer. During the hot-embossing of the first series of 5 µm structure heights samples, the pressure applied during the cooling down was constant and it was removed just before the de-embossing. This pressure was applied for 1 minute at constant temperature, the embossing temperature 175° C., and was removed before the cooling down. These changes were seen to improve the embossing of the problematic 25 µm high structure.

5.1 Surface Characterization

Micro Structures

FIGS. 5A to 5C are microscope images illustrating the micropillars 50 extending from the Optim® surface. FIG. 5A illustrates micropillars with 10 µm average diameter, FIG. 5B illustrates micropillars with 30 µm average diameter and FIG. 5C illustrate micropillars of 10 µm average diameter but with a semi-random pattern.

Figure 6B:
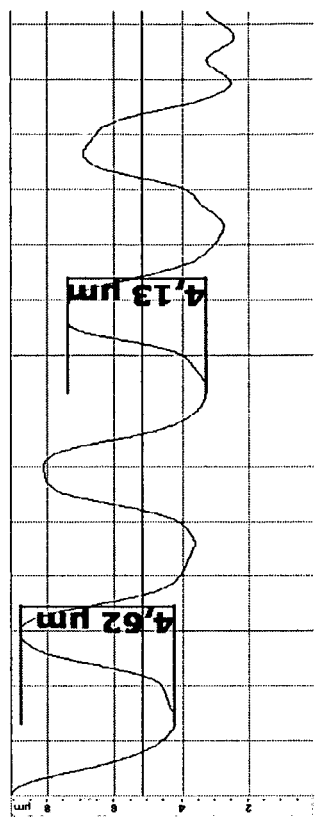
FIGS. 6A and 6B illustrate a topographical image of a pattern of extending micropillars according to an embodiment (FIG. 6A) and a diagram of the profile of the micropillars (FIG. 6B)
Figure 6A:
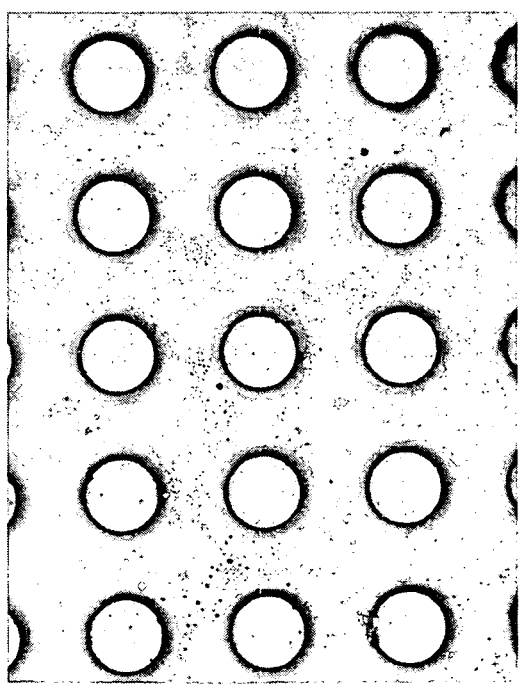
Figure 7:
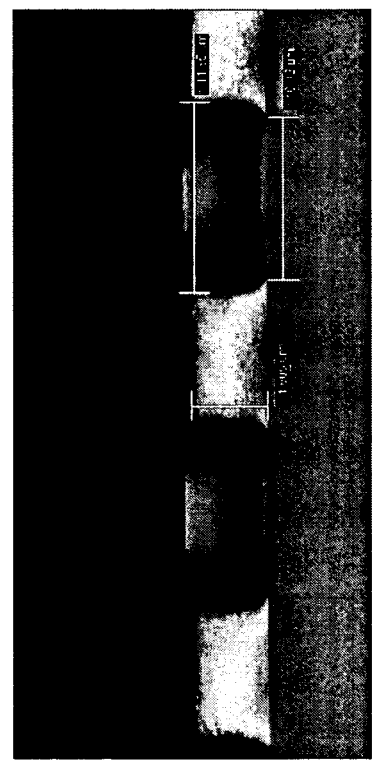
FIG. 7 is a scanning electron microscopy (SEM) image of a template employed for manufacturing a pattern of extending micropillar according to an embodiment.

A topographical image was produced by putting stacks of images at different heights together and by doing this a graph view or a profile could be viewed as well, see FIGS. 6A and 6B. It was determined that the height was around 4.6 µm, which corresponds to the depth of the structures in the template, seen in FIG. 7. The gradient seen in FIG. 6B is because the Optim® piece is not smooth.

5.2 Surface Characterization

Nano Structures

The objective with the two different plasma treatments was to create two distinct nano-topographies upon the surface of the microstructures, and by that creating a hierarchical structure. The surfaces were analyzed by AFM and FIGS. 8A and 8B illustrate the result of the low plasma treatment (ICP power equal to 300 W) and FIGS. 9A and 9B illustrate the results seen with the high plasma treatment (ICP power equal to 500 W).

The low or first plasma treatment, with ICP power of 300 W, produced nanostructures where some of the tops were 250 nm and the roughness (Rq) for such surface was determined to 30.7 nm. The average height of the tops varies between 60 and 100 nm and the width of the tops is around 100 nm.

The high or second plasma treatment, with ICP power of 500 W, produced nanostructure where some of the tops were as high as 450 nm and the roughness (Rq) for such surface was measured to 65.3 nm. The average height of the tops varies between 150 nm and 200 nm and the width was determined to be around 100 nm. The high plasma treatment results in high aspect ratio nanostructure.

Figures 8A, 8B:
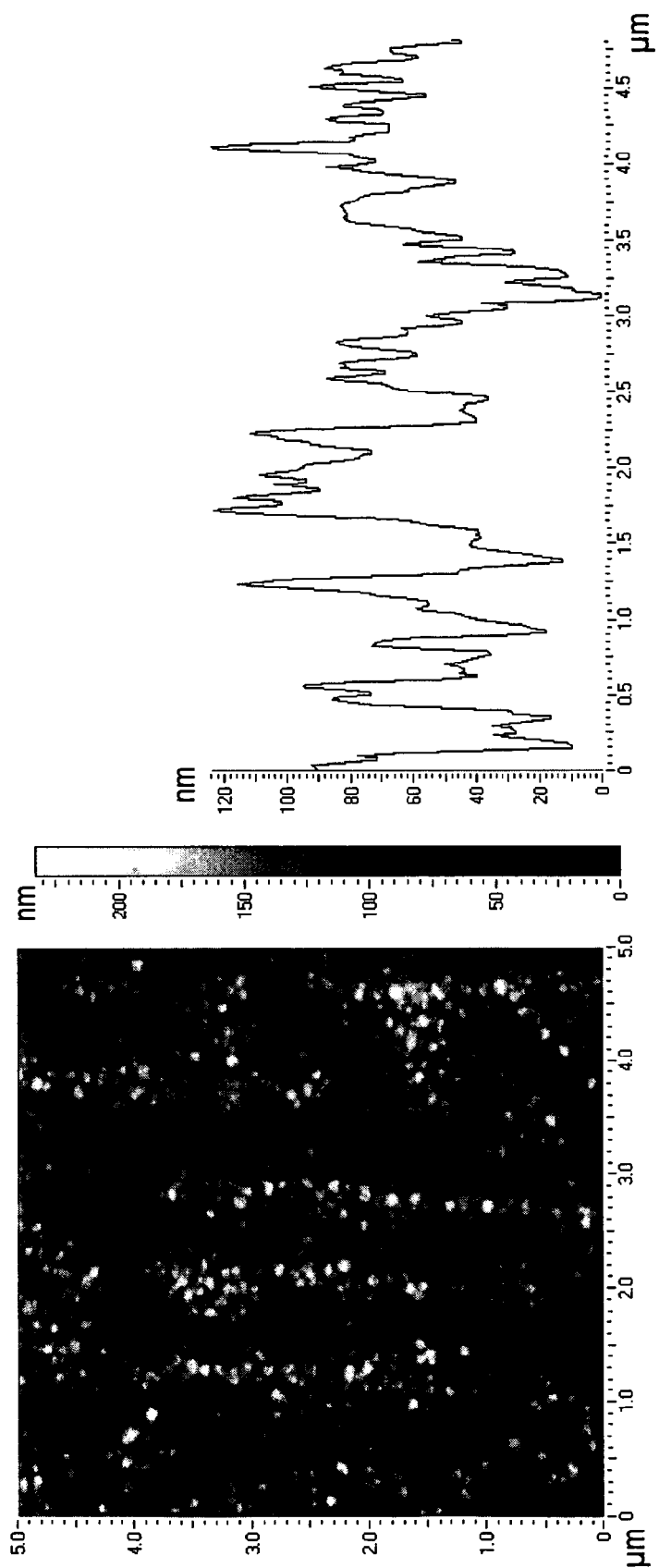
FIGS. 8A and 8B illustrate an atomic force microscopy (AFM) image (FIG. 8A) and the height profile (FIG. 8B) of a nanostructured surface according to an embodiment.
Figures 9A, 9B:
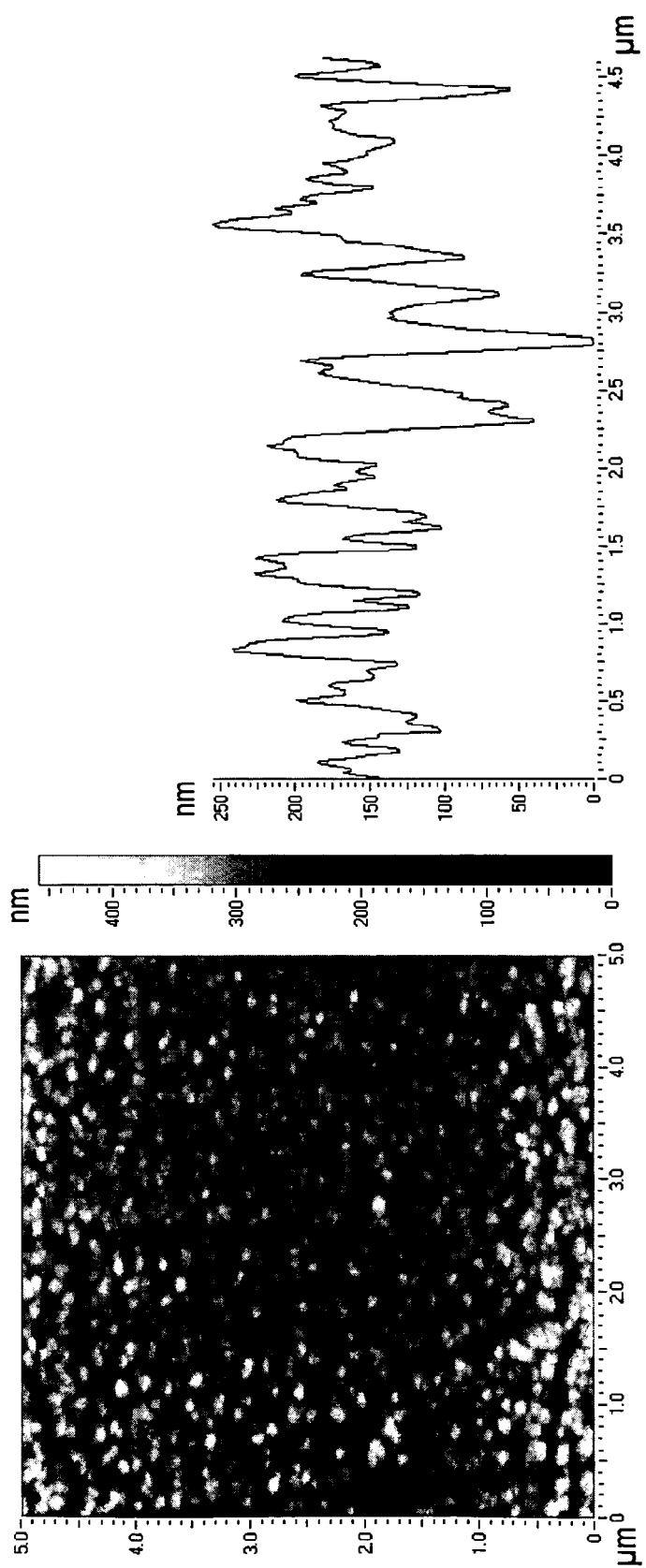
FIGS. 9A and 9B illustrate an AFM image (FIG. 9A) and the height profile (FIG. 9B) of a nanostructured surface according to another embodiment.

In the 2D AFM images of FIGS. 8A and 9A the nanostructures are represented by a variation in grayscale and the bar to the right of the images displays the range in height. The profiles shown in FIGS. 8B and 9B depict how the height changes over a drawn line over the 2D images. Note that the scales are not the same in FIGS. 8B and 9B.

5.3 Final Design Matrix

Table 3 below illustrates the final design matrix of the various Optim® test surfaces that were employed in the protein adsorption and cell adhesion experiments.

TABLE 3

Design matrix

| No. | Height (µm) | Diameter (µm) | Spacing (µm) | Degree of chaos | Nanoheight (rms) |
|---|---|---|---|---|---|
| 1 | 4.6 | 10 | 10 | 0 | 30.7 |
| 2 | 4.6 | 30 | 10 | 0 | 30.7 |
| 3 | 4.6 | 10 | 30 | 0 | 30.7 |
| 4 | 4.6 | 30 | 30 | 0 | 30.7 |
| 5 | 4.6 | 10 | 10 | 0.6 | 30.7 |
| 6 | 4.6 | 30 | 10 | 0.6 | 30.7 |
| 7 | 4.6 | 10 | 30 | 0.6 | 30.7 |
| 8 | 4.6 | 30 | 30 | 0.6 | 30.7 |
| 9 | 4.6 | 10 | 10 | 0 | 65.3 |
| 10 | 4.6 | 30 | 10 | 0 | 65.3 |
| 11 | 4.6 | 10 | 30 | 0 | 65.3 |
| 12 | 4.6 | 30 | 30 | 0 | 65.3 |
| 13 | 4.6 | 10 | 10 | 0.6 | 65.3 |
| 14 | 4.6 | 30 | 10 | 0.6 | 65.3 |
| 15 | 4.6 | 10 | 30 | 0.6 | 65.3 |
| 16 | 4.6 | 30 | 30 | 0.6 | 65.3 |

5.4 Protein Adsorption

TMB undergoes an oxidation and turns blue in the reaction with HRP and the absorbance values are a measure of the amount of TMB that has oxidized and consequently a measure of the amount of protein adsorbed on the different microstructures. Table 4 gives the optical density at 370 nm and 655 nm for each sample and protein type. As a negative control the opposed protein was incubated on a smooth surface and the optical densities are less than 0.2, indicating a low conversion of the TMB. In other words there is a low non-specific binding of the antibodies to the surface and the TMB conversion on the test samples is most probably due to protein adsorbed to the surfaces.

TABLE 4

Protein adsorption

| Sample | Hfg (370 nm) | Hfg (655 nm) | HSA (370 nm) | HSA (655 nm) |
|---|---|---|---|---|
| 1 | 0.45 | 0.72 | 0.48 | 0.74 |
| 2 | 0.55 | 0.81 | 0.46 | 0.70 |
| 3 | 0.43 | 0.65 | 0.44 | 0.66 |
| 4 | 0.37 | 0.59 | 0.41 | 0.61 |
| 5 | 0.52 | 0.79 | 0.38 | 0.56 |
| 6 | 0.50 | 0.75 | 0.47 | 0.79 |
| 7 | 0.36 | 0.55 | 0.22 | 0.32 |
| 8 | 0.51 | 0.79 | 0.42 | 0.63 |
| 9 | 0.66 | 1.03 | 0.63 | 0.95 |
| 10 | 0.40 | 0.63 | 0.35 | 0.51 |
| 11 | 0.57 | 0.89 | 0.51 | 0.76 |
| 12 | 0.59 | 0.93 | 0.56 | 0.84 |
| 13 | 0.49 | 0.73 | 0.41 | 0.61 |
| 14 | 0.51 | 0.92 | 0.54 | 0.81 |

TABLE 4-continued

Protein adsorption

| Sample | Hfg (370 nm) | Hfg (655 nm) | HSA (370 nm) | HSA (655 nm) |
|---|---|---|---|---|
| 15 | 0.57 | 0.86 | 0.31 | 0.45 |
| 16 | 0.60 | 0.91 | 0.56 | 0.84 |
| Positive | 0.70 | 1.20 | 0.30 | 0.44 |
| Negative | 0.09 | 0.12 | 0.13 | 0.19 |

An average of the optical absorbance at 370 nm and 655 nm was calculated and used to evaluate the protein adsorption on the different samples. The results are summarized in FIG. 10, where the protein adsorptions are compared for each sample 1-16 and where each sample number refers to the combination listed in Table 3.

The HSA adsorption is generally lower than the Hfg adsorption and the relative adsorption of the two proteins follows each other with a few exceptions.

Figure 10:
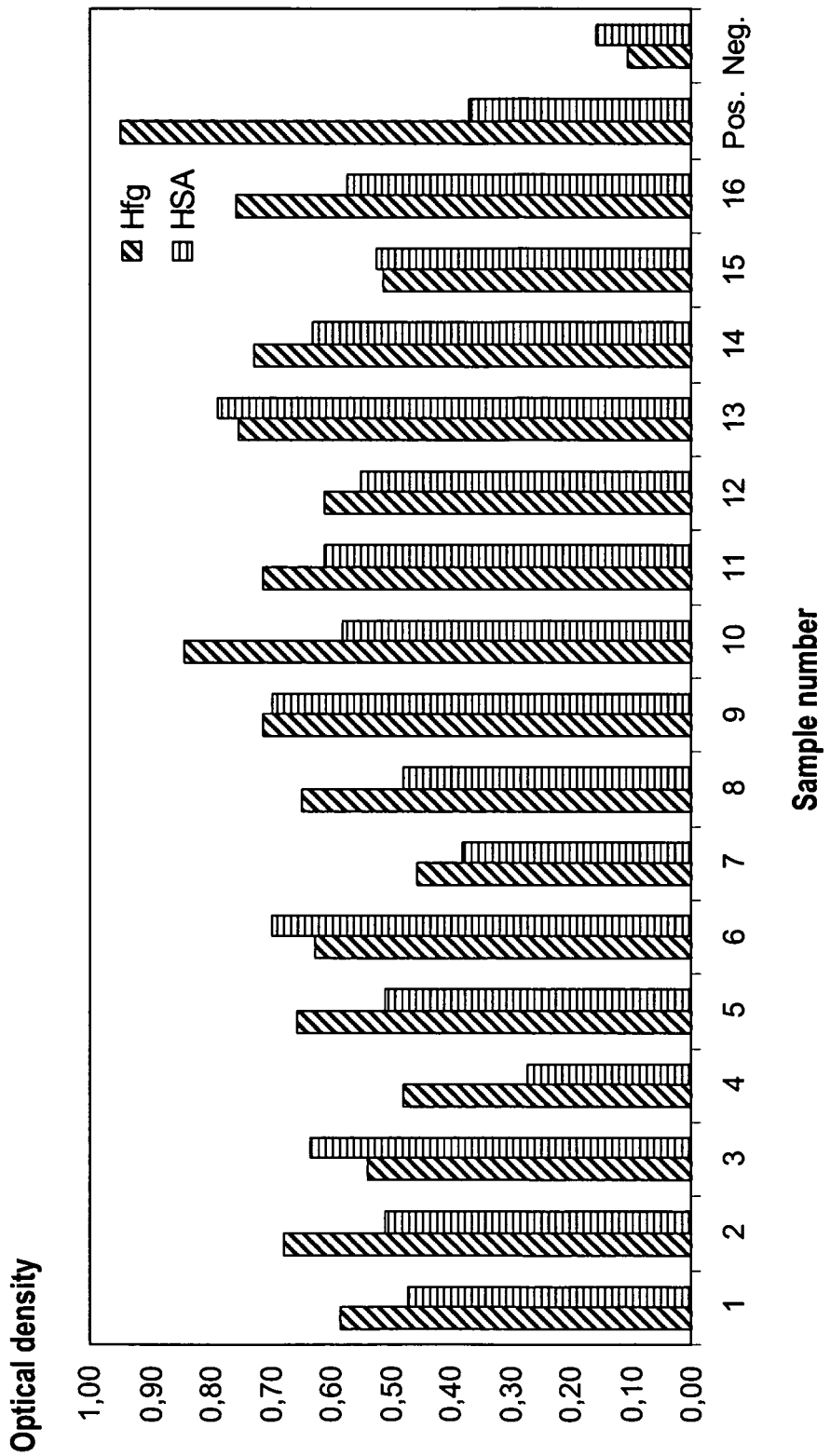
FIG. 10 is a diagram illustrating a comparison of fibrinogen and albumin adsorption onto different patterns of extending microstructures.

Sample numbers 4, 7, 12, and 15 seen in FIG. 10 are found to have lower adsorption than the others. The optical densities for these samples for the Hfg adsorption are 0.48, 0.46, 0.61, 0.52 as compared to sample 10 and the positive control that has 0.85 and 0.95. The samples that are seen to have low protein adsorption have structures where the spacing is 30 µm.

Figure 11:
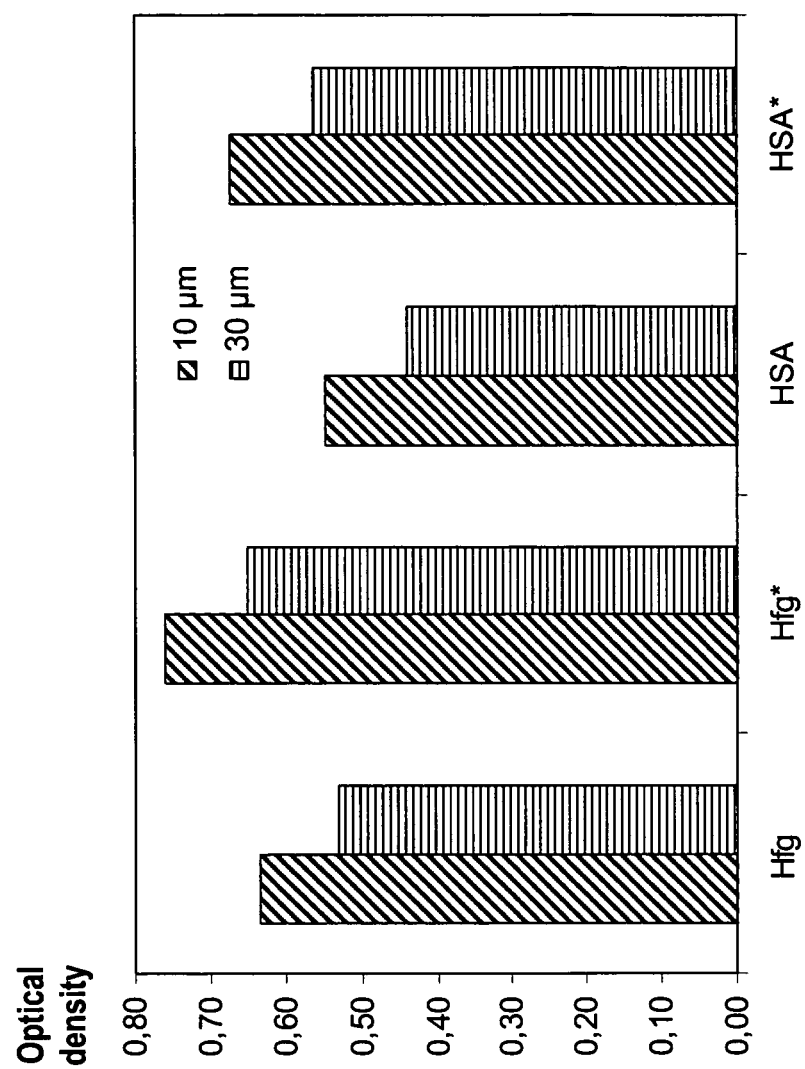
FIG. 11 is a diagram illustrating a comparison of fibrinogen and albumin adsorption onto patterns of extending microstructures having different interpillar spacings.

By comparing all combinations of microstructures having spacing of 30 µm with the corresponding samples having spacing of 10 µm, a clear difference is seen. This effect is illustrated in FIG. 11 where the averages of the optical densities for the combinations of the microstructures having spacing 30 µm respective 10 µm are compared. In FIG. 11 the two different proteins and the two different plasma treatments are distinguished. High plasma treatment is represented by (*) in FIG. 11.

This means that the patterns with 10 µm spacing result in higher protein adsorption. Each of these surfaces has high density of pillars and therefore also higher surface roughness relative to the others. A possible explanation to the differences in protein adsorption between the two spacings could therefore be the difference in surface area and the contact polymer-protein solution.

The roughness factor is calculated as the relation between the actual surface area and the projected area. The surface with pillar size of 10 µm and pillar-pillar distance 10 µm has an increase in surface area of $10 \times \pi \times 4.6$ µm$^2$ for each pillar. Over a projected area of 1 mm$^2$ the total surface area will be 1.36 mm$^2$ and the roughness factor is 1.36.

TABLE 5

Calculated surface roughness

| Microstructure | Roughness factor |
|---|---|
| (10, 10) | 1.36 |
| (30, 10) | 1.27 |
| (10, 30) | 1.09 |
| (30, 30) | 1.12 |

Figure 12:
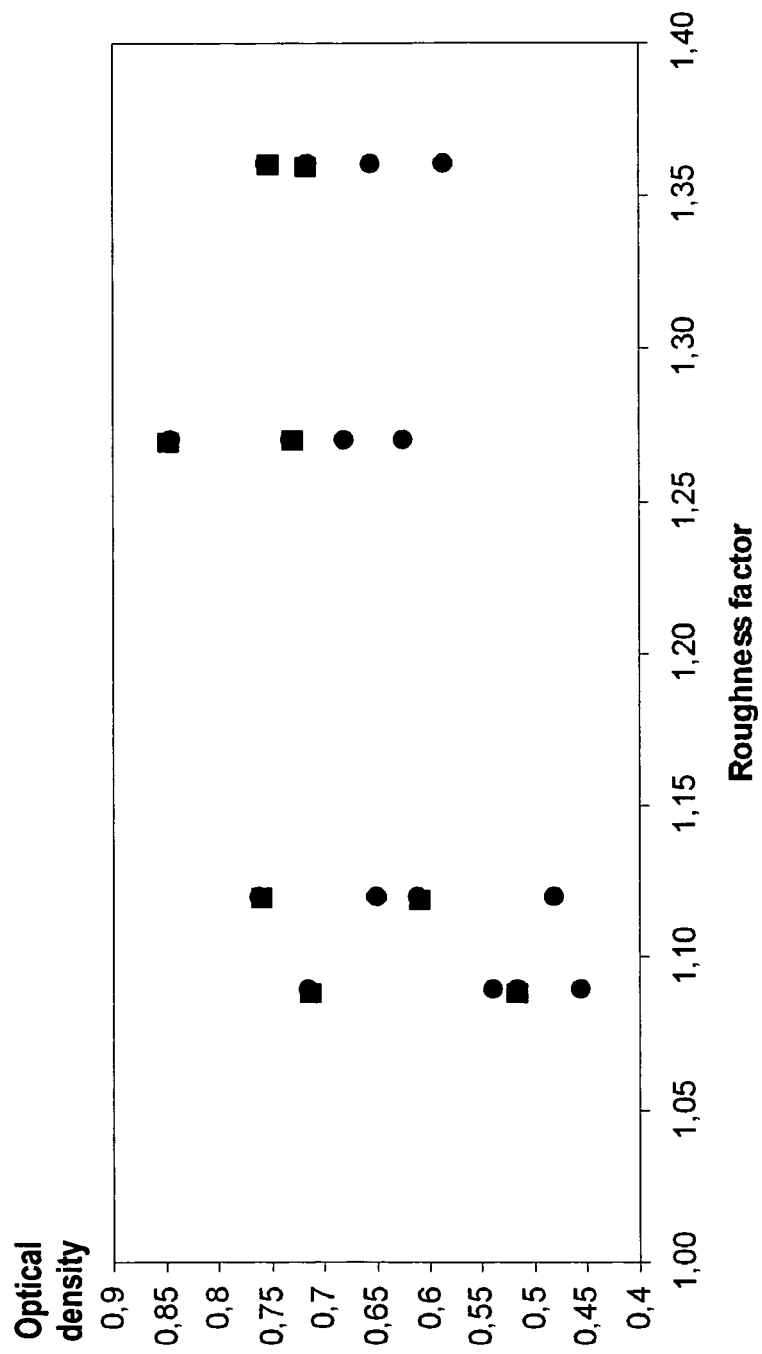
FIG. 12 is a diagram plotting protein adsorption of fibrinogen in relation to surface roughness of different patterns of extending microstructures (filled squares—10 μm interpillar spacing, filled circles—30 μm interpillar spacing)

FIG. 12 plots the optical density versus the surface roughness in order to illustrate the increase in protein adsorption due to increase in surface area. The filled circles in FIG. 12 represent data points from the low plasma treatment and the filled squares represent data points from the high plasma treatment.

The protein adsorption does not linearly increase by the surface roughness, but a relation is seen. As seen in FIG. 12, the protein adsorption increases by an increase in surface roughness, but there is an exception and that is the adsorption for the surfaces with structures of 10 µm diameter and 10 µm spacing where the protein adsorption is lower than the expected.

As pointed out before there is a difference in protein adsorption between the two plasma treatments, which suggests that a similar effect of surface roughness may be true in the case of the nano-dimension as well. The results indicate that the increase in surface roughness causes an increase in protein adsorption. The relation of microstructure and nano-structure with the protein adsorption is the same, but cannot be compared due to the undefined relation between roughness factor (a measure of the increased surface area) and the surface roughness.

In the simplest case of a superhydrophobic surface, the Wenzel state, the liquid conforms to the roughness, which results in an increase in polymer-protein solution contact. So even with a superhydrophobic surface the increase of the surface area will result in increase in the protein adsorption consistent with the results above. In the other case, the Cassie-Baxter state the liquid stays on top of the pillars, which results in that the polymer-protein solution contact is reduced to the top of the pillars. Independently of the state, proteins will be adsorbed to the surface. A possible risk is that the observed hydrophilicity of the adsorbed protein layer will drive the solvent front into the surface structure and the protein solution will penetrate the structure in the same manner as in the Wenzel state. So regardless the initial state of the superhydrophobic surface the polymer-protein solution contact may eventually, in all cases of combinations, be increased due to an increase in surface roughness. This is an increase, which results in an increase in the protein adsorption. However, depending on how stable the superhydrophobic surface is the rate in which the protein adsorption occurs will decrease. This could be the explanation to the deviating result for 10 µm diameter and 10 µm spacing, as it theoretically is the most stable superhydrophobic surface of the tested structured surfaces. By increasing the incubation time, the deviation will possibly diminish and the relation surface area to protein adsorption will become close to linear.

The reduced rate of protein adsorption may have a positive effect on the end application, the originally rapid adsorption of blood plasma proteins that occurs when an implant comes into the body will be slowed down.

Figure 13:
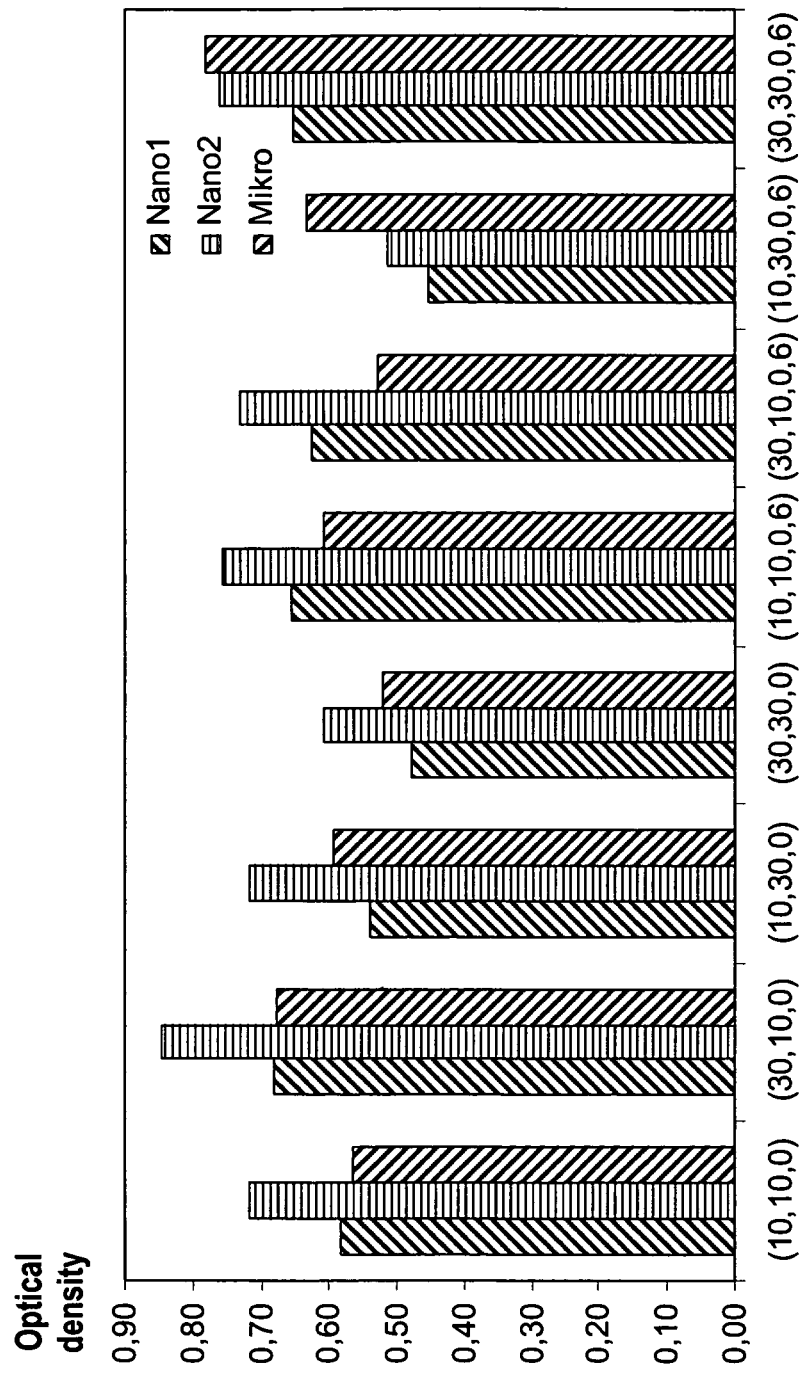
FIG. 13 is a diagram illustrating a comparison in fibrinogen adsorption onto different patterns of extending microstructures.

The change in surface chemistry that the plasma treatment causes will have a positive effect on the inhibition of the fibrinogen adsorption to the Optim® surface. A series of test with micro-structured patterned surface without having any of the plasma treatment was performed in order to compare it with the series of tests with surfaces having the plasma treatments. The results are summarized in FIG. 13. The microstructured samples are found to have similar protein adsorption as the samples having the low or first plasma treatment, denoted Nano1 in FIG. 13. Both of these results in lower adsorptions than the samples having the high or second plasma treatment, denoted Nano2 in FIG. 13. With the earlier reasoning the increase in surface area between the microstructured surface and surfaces having the low plasma treatment would result in an increase in protein adsorption. The use of fluorine-containing plasma in the plasma treatment not only etches the polymer surface but will also produce a surface that is fluorinated. The results suggest that the change in surface chemistry counteracts the effect of the increased surface area and results in similar protein adsorption for the two series of samples.

The results from the protein adsorption can be used to extract the main effects of the diameter, the spacing, degree of chaos and nano-structure. This is done by calculating the average of the responses of low (−) respectively high (+) for each parameter. The calculated average values are seen in Table 6.

TABLE 6

Main effects on protein adsorption

| Parameter | − | + | Slope |
|---|---|---|---|
| Nano | 0.58 | 0.71 | 0.12 |
| Degree of chaos | 0.65 | 0.64 | −0.00 |
| Spacing | 0.70 | 0.59 | −0.11 |
| Diameter | 0.62 | 0.67 | 0.06 |

Figure 14:
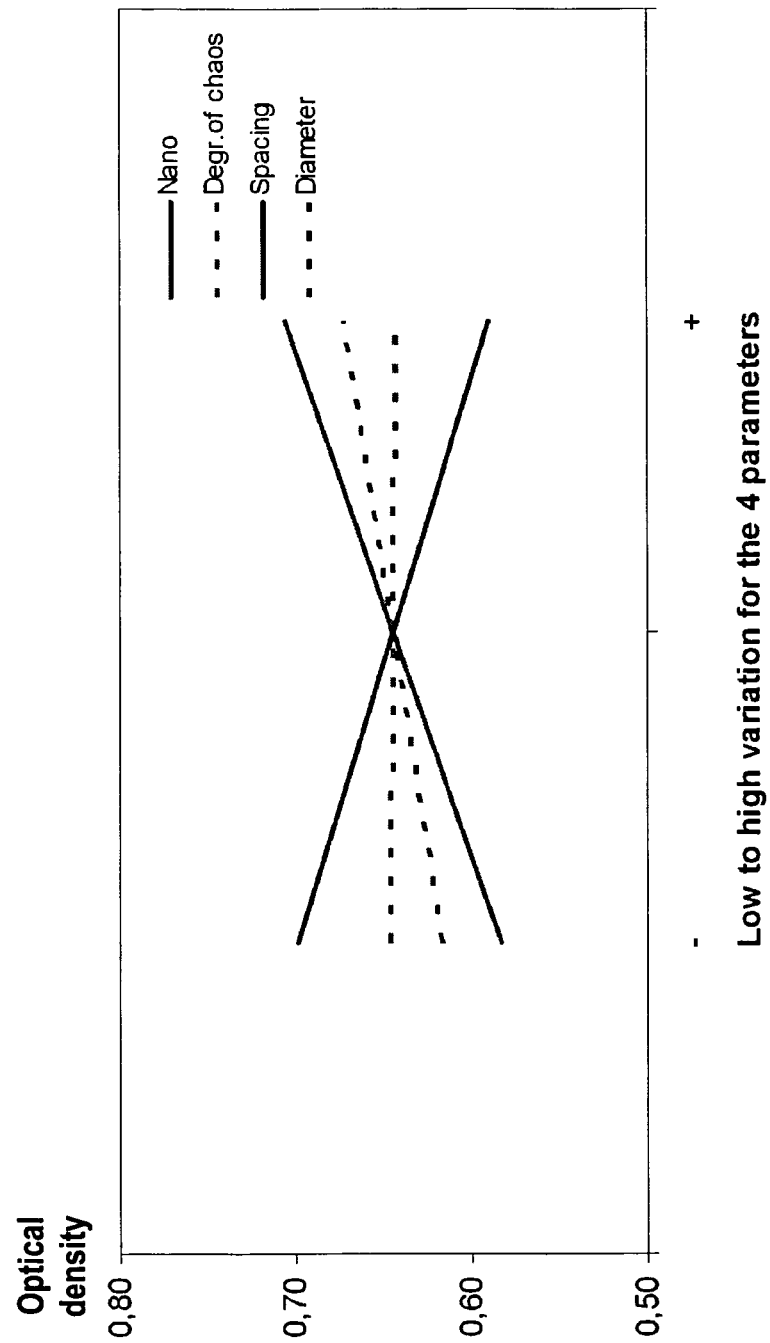
FIG. 14 schematically illustrates the influence of various micropillar parameters on fibrinogen adsorption.

The difference between the high and the low averages determines the magnitude of the effect for that parameter on the protein adsorption. The effect of each parameter is illustrated in FIG. 14. The results indicate that the interpillar spacing and the nano-structure has the largest effects on the protein adsorption.

5.5 Cell Adhesion

Figure 15A:
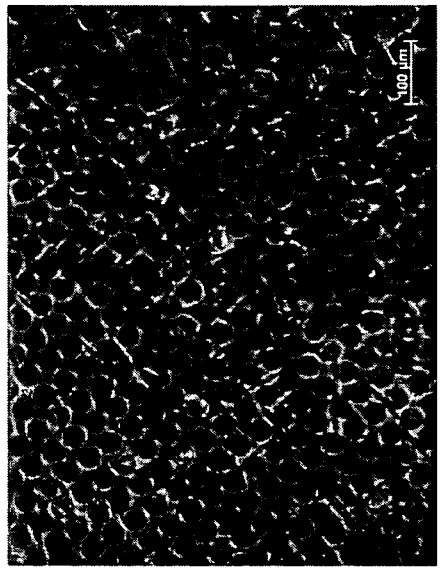
FIGS. 15A to 15F are microscope images of cultured fibroblast cells on surfaces having different patterns of extending micropillars, (diameter, spacing, randomness) FIG. 15A—(10 μm, 10 μm, 0), FIG. 15B (30 μm, 10 μm, 0), FIG. 15C (10 μm, 30 μm, 0), FIG. 15D (30 μm, 30 μm, 0), FIG. 15E (half structured—half smooth) and FIG. 15F (smooth control)
Figure 15B:
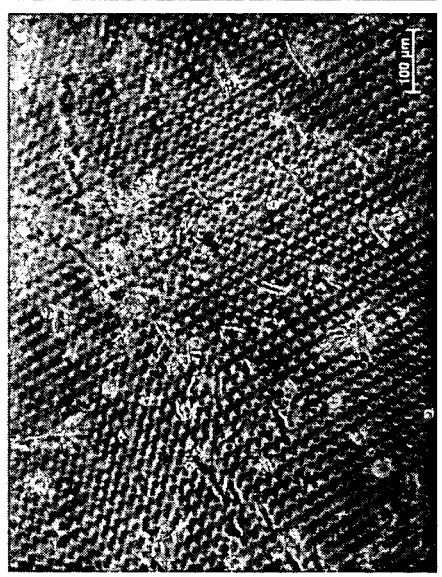
Figure 15C:
Figure 15D:

Microscope images of cultured fibroblast cells were captured and are presented in FIGS. 15A to 15F with variations in (diameter, spacing, degree of chaos): FIG. 15A (10, 10, 0), FIG. 15B (30, 10, 0), FIG. 15C (10, 30, 0), FIG. 15D (30, 30, 0), FIG. 15E (half structured/half smooth) and FIG. 15F (smooth control).

Figures 15E, 15F:
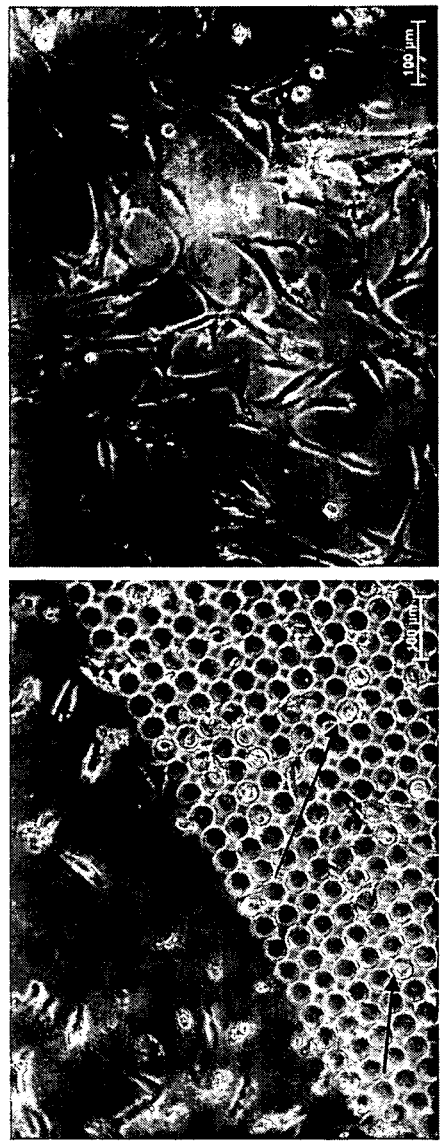

The cells are well spread and take a pyramid shape on the smooth surface (FIG. 15F), which is typical of healthy and proliferative fibroblasts. FIG. 15F, thus, illustrates how the fibroblasts grow and spread on the smooth control sample. The shape of these cells is different from the shape of fibroblasts seen in FIG. 15A, where they are elongated. An elongated cell indicates a cell that is in movement and not comfortable with adhering to the surface. Fibroblasts that cannot adhere to the surface and spread on it will eventually undergo apoptosis and die. Another shape of the fibroblasts that are seen in the images is the spherical shape that for example can be seen in FIG. 15E marked with arrows. Such cells are non-viable.

TABLE 7

Cell counts and cell size on microstructured surfaces

| Micropattern | Cell size (µm$^2$) | Cell counts per 0.6 mm$^2$ |
|---|---|---|
| (10, 10, 0) | 457.2 | 125.7 ± 12.4 |
| (30, 10, 0) | 428.4 | 74.0 ± 22.2 |
| (10, 30, 0) | 912.6 | 88.5 ± 33.2 |
| (30, 30, 0) | 682.2 | 82.3 ± 10.2 |
| (10, 10, 0, 6) | 224.4 | 115.5 ± 6.5 |
| (30, 10, 0, 6) | 494.0 | 60.0 ± 12.5 |
| (10, 30, 0, 6) | 625.5 | 58.5 ± 2.5 |
| (30, 30, 0, 6) | 498.2 | 19.7 ± 8.7 |

Figure 16:
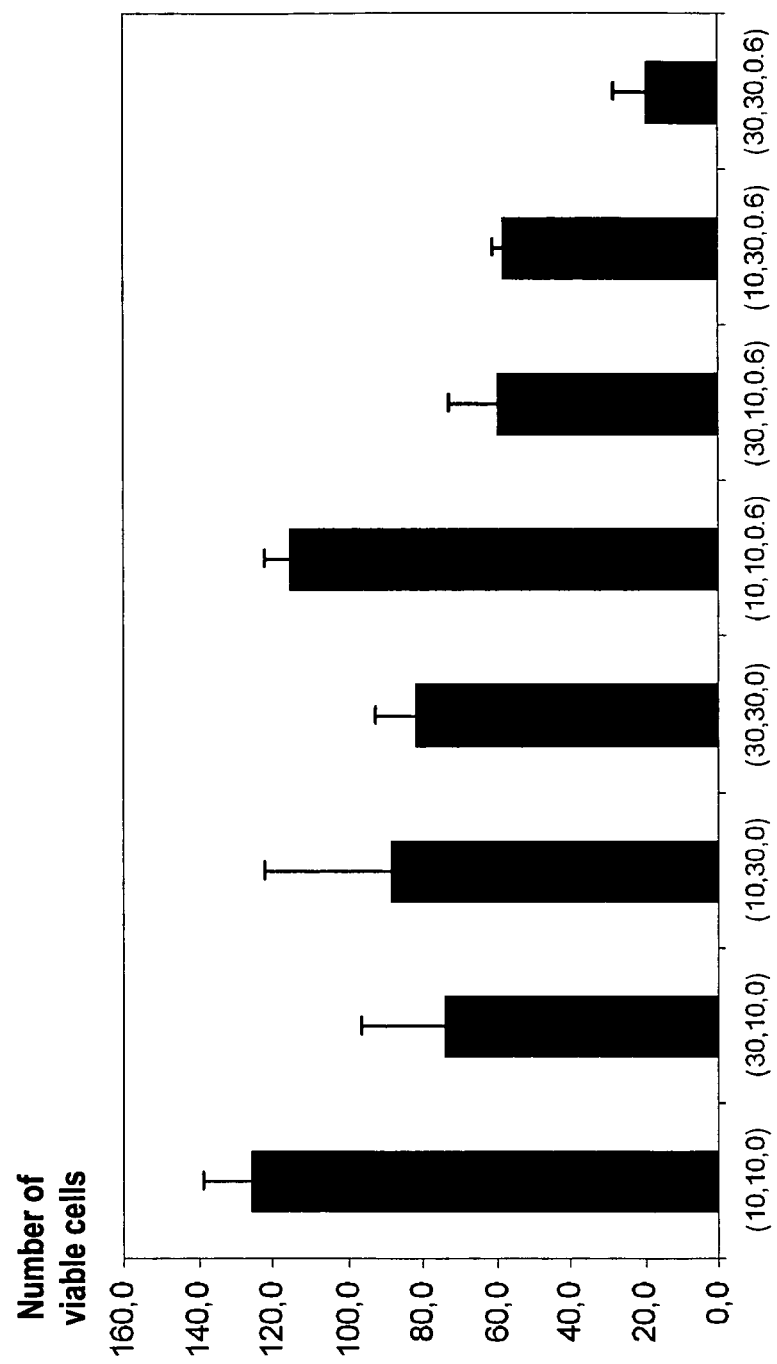
FIG. 16 is a diagram illustrating the number of fibroblast cells on surfaces having different patterns of extending micropillars.
Figure 18:
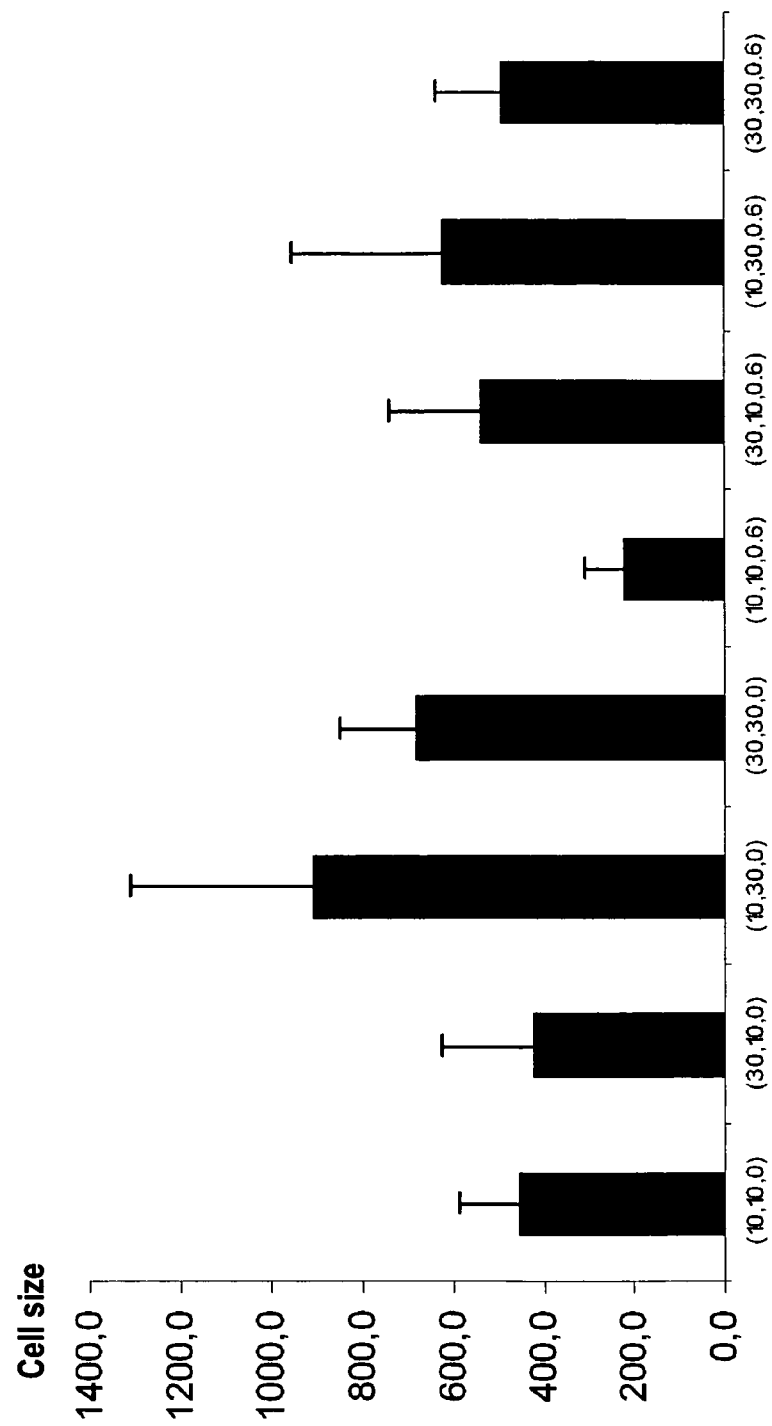
FIG. 18 is a diagram illustrating average cell size on fibroblast cells on surfaces having different patterns of extending micropillars.

The cell size and cell counts were calculated and the values are displayed in Table 7 for all combinations of microstructures. All cells on each image were counted and each image covered an area of 0.6 mm². The results of the cell counts and cell size are summarized in FIG. 16 and FIG. 18.

Figure 17:
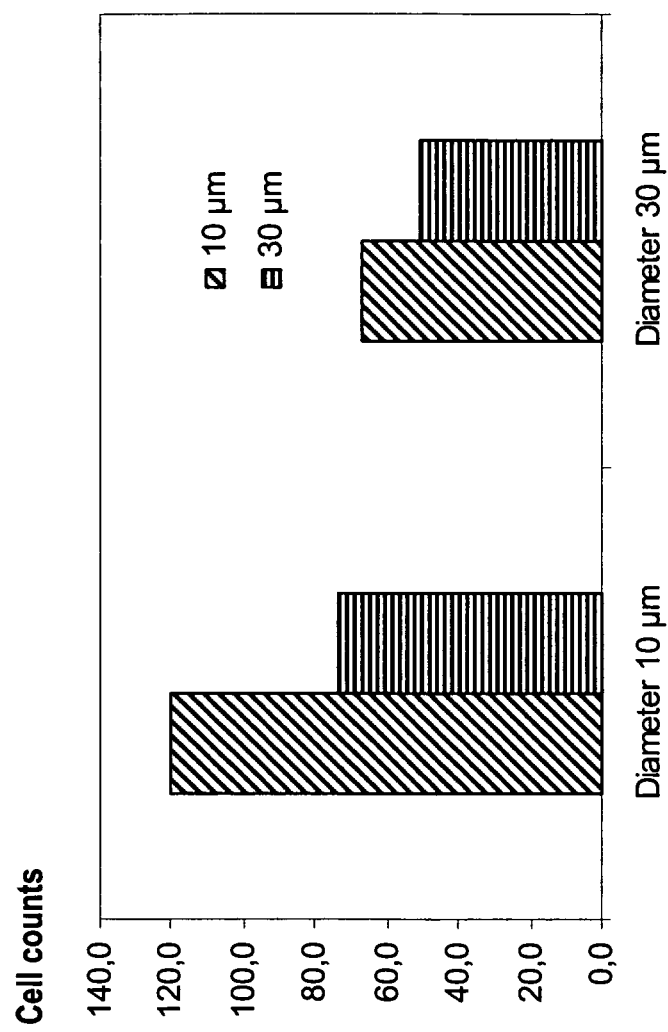
FIG. 17 is a diagram illustrating the difference in cell count of viable cells for different interpillar spacings.

The cell counts are reduced on the patterns where the pillars are 30 µm in diameter and the lowest number of cells is seen on the surfaces with semi-random pillars of 30 µm in diameter and 30 µm in spacing. One of the reasons for this low number is that cells seen on top of these pillars are circular in shape and are therefore not viable. The effect of the spacing and diameter on the cell counts is illustrated in FIG. 17, where the average cell counts for the two spacing and diameter are illustrated. 10 µm spacing has been marked with an inclined pattern, whereas 30 µm spacing has vertical stripes.

A high number of cells are found on the surface with micro-structure 10 µm in diameter and in particular in combination with an interpillar spacing of 30 µm. This particular pattern also has viable fibroblasts with the same kind of pyramid shape seen on the smooth surface, which possibly indicate that the cell will grow and proliferate on these kinds of structured surfaces, i.e. structured surfaces having large spacing. The size of these cells is also found to be larger compared to the other patterned surfaces. However, the structures with 30 µm diameter and 30 µm in interpillar spacing have an area between the pillars that is in the same range as the 10 µm diameter and 30 µm spacing patterns. It was therefore highly surprising that the patterns with the larger pillar diameter significantly reduced the cell adhesion compared to patterns with the lower pillar diameter even if the two patterns have the same interpillar spacings.

The low number of cells on these 30 µm-diameter patterns may be explained by how they react differently to the different sized pillars. On most of the combinations of microstructures the cells were found to attach and extend between the micropillars and not on top of them. This was not the case for the samples where the micropillars had diameter of 30 µm. On these patterns the cells were found to climb up on the micropillars, something that was not seen on the patterns with pillars with diameter of 10 µm. In some of these cases this resulted in a trap for the cells as seen in FIG. 19B marked with black arrow and the cells were caught at the top of the micropillars. It could be possible that when the cells approach the pillar edge from the bottom they are able to attach to the pillar wall, which not is possible if they approach the pillar edge from above.

In other cases the cells were found to extend over more than one pillar, which is seen in FIG. 19B marked by circle. This phenomenon was seen on the patterns where the micropillars were semi-randomly distributed and where the interpillar spacing could be less than 10 µm. This indicates that the µm spacing is a large enough obstacle to prevent the cells to extend over more than one pillar and represents therefore a limit to the cells to attach between the micropillars. To summarize, the cells behave in three different ways on the various patterns. They adhere and extend between the pillars, see FIG. 19A white arrow, they adhere on top of the pillars, see FIG. 19B black arrow and they extend over more than one pillar, see FIG. 19B black circle. So the number of viable attached cells depends in particular on the semi-random arrangement of the micropillars, the diameter of the micropillar and the spacing. A pillar with a diameter of 30 µm, or close to area of the cell, will in some sense induce the cell to attach to the top, which eventually will lead to apoptosis and death for the cell when it is not fully allowed to spread and communicate with other cells in its surrounding.

The results from the cell counts can be used to extract the main effects of the diameter, the spacing and the degree of chaos to the number of viable cells on the surfaces. This is done by calculating the average of the responses of low (−) respectively high (+) for each parameter. The calculated average values are seen in Table 8.

TABLE 8

| Main effects on cell adhesion | | | |
| --- | --- | --- | --- |
| Parameter | − | + | Slope |
| Degree of chaos | 92.60 | 63.42 | −29.19 |
| Spacing | 93.79 | 62.23 | −31.56 |
| Diameter | 97.04 | 58.98 | −38.06 |

Figure 20:
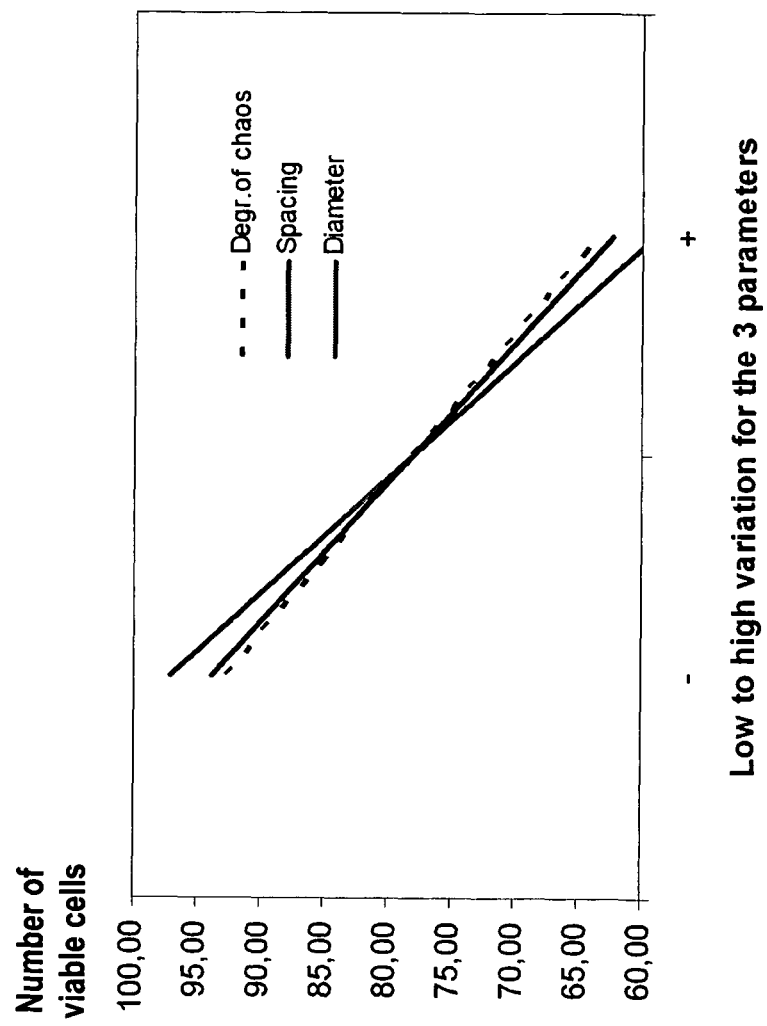
FIG. 20 schematically illustrates the influence of various micropillar parameters on the number of viable fibroblast cells.

All of the parameters seem to have a significant effect on the cell counts, and going from low to high level decreases the number of viable cells. The main effects are illustrated in FIG. 20. In particular, the pillar diameter and also degree of chaos seemed to be important parameters with regard to the number of adhering viable cells.

Figure 21A:
FIGS. 21A and 21B are microscope images of fibroblast cells cultured on smooth surface for 3 days (FIG. 21A) and 7 days (FIG. 21B)
Figure 21B:
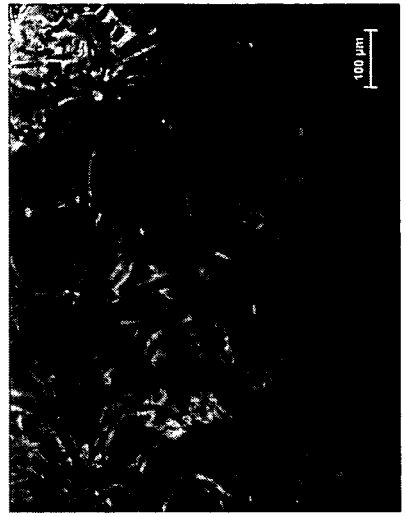
Figure 22A:
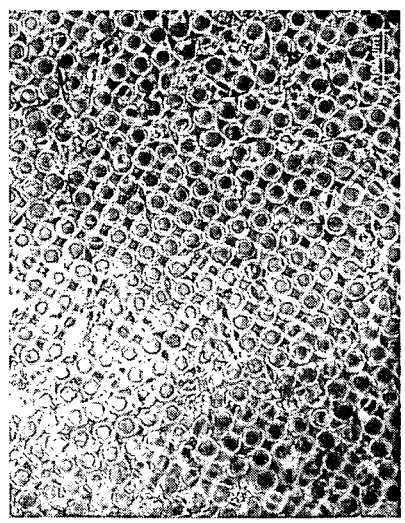
FIGS. 22A and 22B are microscope images of fibroblast cells cultured on a surface with a pattern of extending microstructures (pillar diameter 30 μm, interpillar spacing 10 μm) for 3 days (FIG. 22A) and 7 days (FIG. 22B)
Figure 22B:
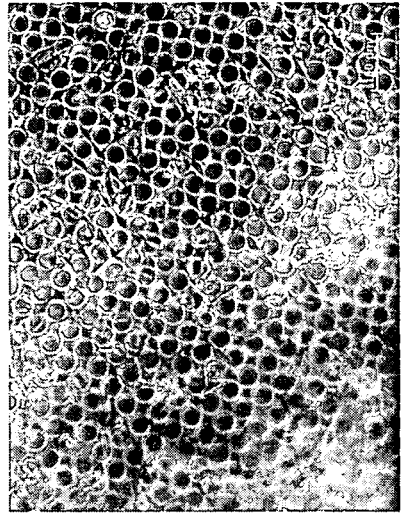

Evaluating the micrographs of the fibroblasts cultured for 3 and 7 days, it is seen that the proliferation is inhibited on the structured surfaces. Images of the smooth control sample were recorded after 3 days in culture and after 7 days in culture and seen in FIGS. 21A (after 3 day) and 21B (after 7 days). The fibroblasts are evenly distributed over the sample, both after 3 days and 7 days in culture. The density of cells is higher after 7 days in culture, which is an indicator that the cells proliferate well on the smooth Optim® surface. Images of a structured surface (diameter 30 µm and spacing 10 µm) were recorded after 3 days in culture (FIG. 22A) and after 7 days in culture (FIG. 22B). The fibroblasts are evenly distributed over the sample, both after 3 days and 7 days in culture. The density of cells is, in contrast to the smooth control in FIGS. 21A and 21B, not higher after 7 days in culture but just about the same. A result that indicates that the cells proliferate less well on structured surfaces.

Figure 23A:
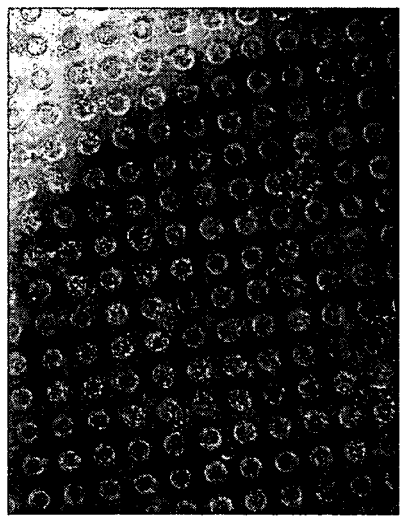
FIGS. 23A and 23B are microscope images of platelet adhesion on surfaces having different patterns of extending microstructures.
Figure 23B:
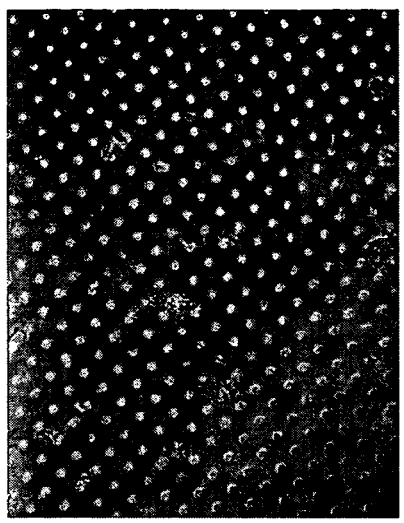

The adsorption of fibrinogen to the surface has in several other studies been shown to correlate with the platelet response to the surface. FIGS. 23A and 23B show images of the adhered platelets to surface with the highest adsorption of proteins and the lowest adsorption of protein. The adsorption of fibrinogen to the smooth surface is seen to be high and the aggregates of platelets are evenly distributed over the whole surface (data not shown). Looking at the micrographs of the patterned samples in FIGS. 23A and 23B, clusters of aggregates are seen and more platelets are found to adhere on top of the pillars rather than in the interspacing between the pillars. The fibrinogen adsorption is thought to start on top of the pillars, and then continue also in the spacing between the pillars and could be a reason for the higher extent of attached platelets on top of the pillars.

6 Conclusions

The conclusions from the experimental results are presented below.

6.1 Conclusions

Protein Adsorption

The protein adsorption depends on the contact area between polymer and protein solution. The more contact there is the higher the adsorption of proteins will be. Introducing a microstructure on the polymer surface will directly increase such a contact area, but depending on the stability of the superhydrophobic surface the rate at which the protein adsorption occurs will decrease. The surface chemistry is also an important factor.

The 30 μm spacing gives lower protein adsorption compared to the 10 μm spacing, probably due to the differences in surface area. A high density of pillars (diameter 10 μm and spacing 10 μm), give, relative to the expected increase in protein adsorption with respect to the increase in surface area, a lower protein adsorption. A hierarchical structure formed by additional plasma treatment results in a decrease in protein adsorption.

6.2 Conclusions

Cell Adhesion

Introducing a microstructure on the polymer surface decreases the proliferation of fibroblasts and also results in a lower amount of healthy and viable fibroblasts adhered to the surface. A pillar size close to the area of the cell reduces the number of viable cells on the surfaces. A pillar with a diameter of 30 μm makes it possible for the cells to adhere on top of the pillars, but makes it impossible for the cells to spread and communicate with other cells. This reduces the number of viable cells. A pillar with a diameter of 10 μm does not allow the cells to adhere on top of pillars and the cells adhere between the pillars. This does not reduce the number of viable cells. A pillar to pillar spacing less than the size of the cells reduces the number of cell adhered to surfaces. A spacing of 10 μm between the pillars prevents the cells from spreading, which eventually results in a reduced number of viable cells. A spacing of 30 μm is large enough to allow the cells to spread between the pillars. Using a semi-random pattern of micropillars seems to reduce the number of viable cells.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

The invention claimed is:

1. An implantable device comprising:
a structure made of a material selected from silicone, polyurethane and combinations thereof and having a surface facing surrounding tissue when the implantable device is implanted in a subject body;
wherein at least a portion of the surface of the structure has a semi-random pattern of extending micropillars where the coordinates of a micropillar number i on the surface are defined as $(x_i, y_i)=(x_i^0+\alpha_i+\zeta \times s, y_i^0 \times \beta_i \zeta \times S)$ wherein $\alpha_i, \beta_i$ are random numbers within a range of 0 to 1, S denotes an average interpillar spacing in the semi-pattern of micropillars, $\zeta$ is within a range of 0.5 to 0.7 and $(x_i^0, y_i^0)$ indicates the coordinates of the micropillar number i in a perfectly ordered array of extending micropillars with interpillar spacings equal to S.

2. The implantable device according to claim 1, wherein $\zeta=0.6$.

3. An implantable device comprising:
a structure made of a material selected from silicone, polyurethane and combinations thereof and having a surface facing surrounding tissue when the implantable device is implanted in a subject body;
wherein at least a portion of the surface of the structure has a semi-random pattern of extending micropillars where the coordinates of a micropillar number i on the surface are defined as $(x_i, y_i)=(x_i^0+\alpha_i \times \zeta \times s, y_i^0+\beta_i \times \zeta \times S)$, wherein $\alpha_i, \beta_i$ are random numbers within a range of 0 to 1, S denotes an average interpillar spacing in the semi-pattern of micropillars, $\zeta$ is within a range of 0.2 to 0.9 and $(x_i^0, y_i^0)$ indicates the coordinates of the micropillar number i in a perfectly ordered array of extending micropillars with interpillar spacings equal to S; and
wherein a distance between the coordinates $(x_i, y_i)$ of the micropillar number i on the surface and coordinates of a closest neighboring micropillar on the surface is larger than an average pillar diameter or an average pillar side lengths of the micropillars.

4. An implantable device comprising:
a structure made of a material selected from silicone, polyurethane and combinations thereof and having a surface facing surrounding tissue when the implantable device is implanted in a subject body;
wherein at least a portion of the surface of the structure has a semi-random pattern of extending micropillars where the coordinates of a micropillar number i on the surface are defined as $(x_i, y_i)=(x_i^0+\alpha_i \times \zeta \times s, y_i^0+\beta_i \times \zeta \times S)$ wherein $\alpha_i, \beta_i$ are random numbers within a range of 0 to 1, S denotes an average interpillar spacing in the semi-pattern of micropillars, $\zeta$ is within a range of 0.2 to 0.9 and $(x_i^0, y_i^0)$ indicates the coordinates of the micropillar number i in a perfectly ordered array of extending micropillars with interpillar spacings equal to S; and
wherein the random numbers $\alpha_i, \beta_i$ follow a normal distribution implying that values around 0 are generated more often as compared to values close to 1.

5. An implantable device comprising:
a structure made of a material selected from silicone, polyurethane and combinations thereof and having a surface facing surrounding tissue when the implantable device is implanted in a subject body;
wherein at least a portion of the surface of the structure has a semi-random pattern of extending micropillars where the coordinates of a micropillar number i on the surface are defined as $(x_i, y_i)=(x_i^0+\alpha_i+\zeta \times s, y_i^0+\beta_i \times \zeta \times S)$ wherein $\alpha_i, \beta_i$ are random numbers within a range of 0 to 1, S denotes an average interpillar spacing in the semi-pattern of micropillars, $\zeta$ is within a range of 0.2 to 0.9 and $(x_i^0, y_i^0)$ indicates the coordinates of the micropillar number i in a perfectly ordered array of extending micropillars with interpillar spacings equal to S; and
wherein the micropillars have an average interpillar spacing within a range of 5 μm to 40 μm, preferably within a range of 10 μm to 30 μm, and more preferably an average interpillar spacing of 30 μm.

6. An implantable device comprising:
a structure made of a material selected from silicone, polyurethane and combinations thereof and having a surface facing surrounding tissue when the implantable device is implanted in a subject body;
wherein at least a portion of the surface of the structure has a semi-random pattern of extending micropillars where the coordinates of a micropillar number i on the surface are defined as $(x_i, y_i)=(x_i^0+\alpha_i \times \zeta \times s, y_i^0+\beta_i \times \zeta \times S)$, wherein $\alpha_i, \beta_i$ are random numbers within a range of 0 to 1, S denotes an average interpillar spacing in the semi-pattern of micropillars, $\zeta$ is within a range of 0.2 to 0.9 and $(x_i^0, y_i^0)$ indicates the coordinates of the micropillar number i in a perfectly ordered array of extending micropillars with interpillar spacings equal to S; and wherein the implantable device is an implantable medical lead comprising:
an electrode arranged in connection with a distal portion of the implantable medical lead;
an electrode terminal arranged in connection with an opposite, proximal portion of the implantable medical lead, wherein the proximal portion is configured to be connected to an implantable medical device;
a conductor having a first end connected to electrode and a second, opposite end connected to the electrode terminal; and
an insulating tubing having a bore through which the conductor is running, wherein the insulating tubing is made of a material selected from silicone, polyurethane and combinations thereof, wherein at least a portion of a lateral surface of the insulating tubing has the semi-random pattern of extending micropillars.

7. An implantable device comprising:
a structure made of a co-polymer of silicone and polyurethane and having a surface facing surrounding tissue when the implantable device is implanted in a subject body;
wherein at least a portion of the surface of the structure has a semi-random pattern of extending micropillars where the coordinates of a micropillar number i on the surface are defined as $(x_i, y_i) = (x_i^0 + \alpha_i \times \zeta \times s, y_i^0 + \beta_i \times \zeta \times S)$, wherein $\alpha_i, \beta_i$ are random numbers within a range of 0 to 1, S denotes an average interpillar spacing in the semi-pattern of micropillars, $\zeta$ is within a range of 0.2 to 0.9 and $(x_i^0, y_i^0)$ indicates the coordinates of the micropillar number i in a perfectly ordered array of extending micropillars with interpillar spacings equal to S.

8. The implantable device according to claim 7, wherein the co-polymer of silicone and polyurethane comprises 45 to 50% by weight, preferably about 48% by weight, of silicone, 37.5 to 42.5% by weight, preferably about 40% by weight, of polyurethane and 9.5 to 14.5% by weight, preferably about 12% by weight, of polyhexamethylene oxide.

9. The implantable device according to claim 7, wherein the co-polymer of silicone and polyurethane is a co-polymer of silicone, polyurethane and polycarbonate.

10. An implantable device comprising:
a structure made of a material selected from silicone, polyurethane and combinations thereof and having a surface facing surrounding tissue when the implantable device is implanted in a subject body;
wherein at least a portion of the surface of the structure has a semi-random pattern of extending micropillars where the coordinates of a micropillar number i on the surface are defined as $(x_i, y_i) = (x_i^0 + \alpha_i \times \zeta \times s, y_i^0 + \beta_i \times \zeta \times S)$ wherein $\alpha_i, \beta_i$ are random numbers within a range of 0 to 1, S denotes an average interpillar spacing in the semi-pattern of micropillars, $\zeta$ is within a range of 0.2 to 0.9 and $(x_i^0, y_i^0)$ indicates the coordinates of the micropillar number i in a perfectly ordered array of extending micropillars with interpillar spacings equal to S; and
wherein the micropillars have an average pillar height within a range of 2.5 μm to 30 μm, preferably within a range of 4 μm to 25 μm, and more preferably within a range of 4 μm to 5 μm.

11. An implantable device comprising:
a structure made of a material selected from silicone, polyurethane and combinations thereof and having a surface facing surrounding tissue when the implantable device is implanted in a subject body;
wherein substantially the whole surface of the structure has a semi-random pattern of extending micropillars where the coordinates of a micropillar number a on the surface are defined as $(x_i, y_i) = (x_i^0 + \alpha_i \times \zeta \times s, y_i^0 + \beta_i \times \zeta \times S)$ wherein $\alpha_i, \beta_i$ are random numbers within a range of 0 to 1, S denotes an average interpillar spacing in the semi-pattern of micropillars, $\zeta$ is within a range of 0.2 to 0.9 and $(x_i^0, y_i^0)$ indicates the coordinates of the micropillar number i in a perfectly ordered array of extending micropillars with interpillar spacings equal to S.

12. An implantable device comprising:
a structure made of a material selected from silicone, polyurethane and combinations thereof and having a surface facing surrounding tissue when the implantable device is implanted in a subject body;
wherein at least a portion of the surface of the structure has a semi-random pattern of extending micropillars where the coordinates of a micropillar number i on the surface are defined as $(x_i, y_i) = (x_i^0 + \alpha_i \times \zeta \times s, y_i^0 + \beta_i \times \zeta \times S)$, wherein $\alpha_i, \beta_i$ are random numbers within a range of 0 to 1, S denotes an average interpillar spacing in the semi-pattern of micropillars, $\zeta$ is within a range of 0.2 to 0.9 and $(x_i^0, y_i^0)$ indicates the coordinates of the micropillar number i in a perfectly ordered array of extending micropillars with interpillar spacings equal to S; and
wherein the semi-random pattern is a hierarchical semi-random pattern of the micropillars and nanostructures formed on and extending from the micropillars, wherein the nanostructures have an average height within a range of 20 nm to 140 nm, preferably within a range of 60 nm to 100 nm.

* * * * *